(12) United States Patent
Horino et al.

(10) Patent No.: US 8,748,629 B2
(45) Date of Patent: Jun. 10, 2014

(54) PHOTOCHROMIC MATERIAL

(75) Inventors: Takeru Horino, Tokyo (JP); Atsuhiro Tokita, Tokyo (JP); Toyoji Oshima, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 13/807,461

(22) PCT Filed: Jul. 8, 2011

(86) PCT No.: PCT/JP2011/065702
§ 371 (c)(1),
(2), (4) Date: Dec. 28, 2012

(87) PCT Pub. No.: WO2012/005354
PCT Pub. Date: Jan. 12, 2012

(65) Prior Publication Data
US 2013/0102775 A1 Apr. 25, 2013

(30) Foreign Application Priority Data

| Jul. 9, 2010 | (JP) | 2010-157036 |
| Mar. 31, 2011 | (JP) | 2011-080843 |
| Mar. 31, 2011 | (JP) | 2011-080844 |

(51) Int. Cl.
*C07D 487/04* (2006.01)
*C07D 487/10* (2006.01)
*C07D 487/20* (2006.01)

(52) U.S. Cl.
CPC ............ *C07D 487/04* (2013.01); *C07D 487/10* (2013.01); *C07D 487/20* (2013.01)
USPC ........................................ 548/301.1; 540/543

(58) Field of Classification Search
CPC ... C07D 487/04; C07D 487/10; C07D 487/20
USPC ........................................ 548/301.1; 540/543
See application file for complete search history.

(56) References Cited

U.S. PATENT DOCUMENTS

2012/0245317 A1    9/2012   Abe et al.

FOREIGN PATENT DOCUMENTS

| JP | 4-128834 | 4/1992 |
| JP | 7-9766 | 1/1995 |
| JP | 2009-62344 | 3/2009 |
| JP | 4643761 | 3/2011 |
| JP | 2011-132265 | 7/2011 |
| JP | 2011-144289 | 7/2011 |
| WO | 2010/061579 | 6/2010 |

OTHER PUBLICATIONS

Search report from International Application No. PCT/JP2011/065702, mail date is Sep. 20, 2011.
Kunihiro Ichimura, "Development of Photochromic Materials", CMC Publishing Co., Ltd., 2009, pp. 1-80.
"Journal of the American Chemical Society 131 (12)", 2009, pp. 4227-4229.
"Journal of Physical Chemistry Letters, 1(7)", Mar. 16, 2010, pp. 1112-1115.
"Macromelecules, 43(8)", Mar. 26, 2010, pp. 3764-3769.

*Primary Examiner* — Laura L. Stockton
(74) *Attorney, Agent, or Firm* — Greenblum & Bernstein, P.L.C.

(57) ABSTRACT

The present invention is a photochromic material formed of a biimidazole compound represented by general formula (1-1):

[Chemical Formula 1]

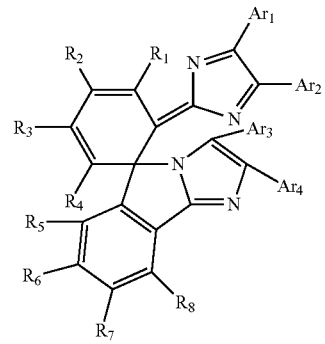

(1-1)

(where, $R_4$ and $R_5$ respectively and independently represent a halogen atom or alkyl group, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, $Ar_1$ to $Ar_4$ respectively and independently represent a substituted or unsubstituted aryl group, $R_4$ may form a condensed, substituted or unsubstituted aryl ring with $R_3$, and $R_5$ may form a condensed, substituted or unsubstituted aryl ring with $R_6$).

8 Claims, 16 Drawing Sheets

GENERAL FORMULA (3-1)

GENERAL FORMULA (1-1)

PHOTOCHROMIC MATERIAL

TECHNICAL FIELD

The present invention relates to a photochromic material, and more particularly, to a photochromic material formed of a novel biimidazole compound.

BACKGROUND ART

Photochromic materials are typically materials that have a function (light modulation function) that enables them to reversibly change color (visible light transmittance) as a result of undergoing an isomerization reaction when irradiated with light, and not only materials prior to being irradiated with light, but also materials formed after being irradiated with light, are referred to as photochromic materials. Consequently, photochromic materials are used as eyeglasses for preventing glare, optical switches as well as display materials such as ink having the ability to switch between display and non-display status. In addition, research is also proceeding on their application to optical discs and other recording materials as well as holograms.

Changes in color demonstrated by photochromic materials are typically expressed as a reversible chemical reaction of a material that is induced when the material is irradiated with light. Typical known examples of photochromic materials include spiropyran-based compounds, spirooxadine-based compounds, naphthopyran-based compounds, fulgide-based compounds, and diarylethene-based compounds (see, for example, Non-Patent Document 1). In addition, compounds having a novel structure that demonstrate rapid photoreactivity have also been recently reported (see, for example, Non-Patent Document 2).

Photochromic materials are broadly divided into those that exhibit a phenomenon referred to as positive photochromism, which causes these materials to change from an uncolored form to a colored form (colored state) accompanying a structural change when irradiated with light, and those that exhibit a phenomenon referred to as negative photochromism (reverse photochromic materials), which causes these materials to conversely change from a colored form (colored state) to an uncolored form when irradiated with light.

Several examples of these reverse photochromic materials have been reported, including spirobenzopyran derivatives (Patent Document 1), dimethyldihydropyrene derivatives (Patent Document 2), and diarylethene derivatives (Patent Document 3).

PRIOR ART DOCUMENTS

Non-Patent Documents

Non-Patent Document 1: "Development of Photochromic Materials", Kunihiro Ichimura, ed., CMC Publishing Co., Ltd., publisher (p. 1-80)
Non-Patent Document 2: Journal of the American Chemical Society, 131 (12), pp. 4227-4229 (2009)

Patent Documents

Patent Document 1: Japanese Patent Application Laid-open No. H4-128834
Patent Document 2: Japanese Patent Application Laid-open No. H7-009766
Patent Document 3: Japanese Patent Application Laid-open No. 2009-062344

SUMMARY OF THE INVENTION

Problems to be Solved by the Invention

By the way, a photochromic function is required to have properties such as color, color optical density or color development rate that are suitable for the particular application thereof. Consequently, it is necessary to develop various types of derivatives and compounds having novel molecular frameworks.

Thus, photochromic materials are being sought that have a novel structure.

An object of the present invention is to provide a photochromic material having a novel structure that demonstrates a reversible structural change (color change) as a result of being irradiated with light or allowing to stand while protected from light after having been irradiated with light.

Means for Solving the Problems

As a result of conducting extensive studies to solve the above-mentioned problems, the inventors of the present invention discovered a completely novel photochromic molecule.

More specifically, the inventors of the present invention discovered a novel compound that demonstrates negative photochromism by using biimidazole for the basic framework and introducing a bulky substituent in $R_4$ and $R_5$ of general formula (1-1). This molecule was in a colored form when in a stable state or initial state, and demonstrated photochromic properties that cause it to isomerize to an uncolored form when irradiated with visible light (reverse photochromic properties).

[Chemical Formula 1]

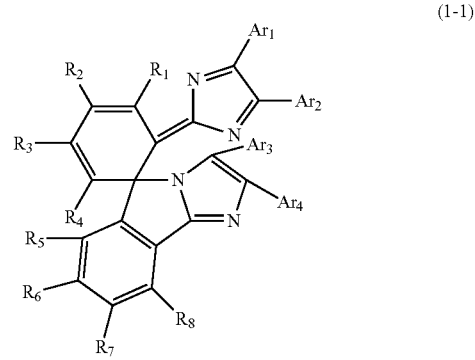

(1-1)

(In the formula, $R_4$ and $R_5$ respectively and independently represent a halogen atom or alkyl group, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, $Ar_1$ to $Ar_4$ respectively and independently represent a substituted or unsubstituted aryl group, $R_4$ may form a condensed, substituted or unsubstituted aryl ring with $R_3$, and $R_5$ may form a condensed, substituted or unsubstituted aryl ring with $R_6$.)

Namely, the present invention is a photochromic material formed of a biimidazole compound represented by the above-mentioned general formula (1-1).

As shown in FIG. 1, the photochromic material of the present invention represented by general formula (1-1) is able to change to an isomer represented by general formula (3-1) as a result of being irradiated with light. Here, the photochromic material represented by general formula (1-1) is a colored form and has low transmittance. On the other hand, the isomer represented by general formula (3-1) is an uncolored form. Thus, according to the photochromic material of the present invention, the color tone of the photochromic material can be adjusted by irradiating with light. The photochromic material of the present invention represented by general formula (1-1) changes from a colored form to an uncolored form as a result of being irradiated with light. Namely, the photochromic material of the present invention represented by general formula (1-1) is a reverse photochromic material. Furthermore, in FIG. 1, Δ indicates thermal energy. However, among those photochromic materials of the present invention represented by general formula (1-1), those photochromic materials in which $R_4$ forms a condensed, substituted or unsubstituted aryl ring with $R_3$ and $R_5$ forms a condensed, substituted or unsubstituted aryl ring with $R_6$ in general formula (1-1) can normally become an isomer represented by general formula (3-1) as a result of being irradiated with light as shown in FIG. 3. However, such photochromic materials do not become an isomer (II) shown in FIG. 1 even if allowed to stand in a state protected from light (see FIG. 3).

In addition, the inventors of the present invention discovered a novel compound that demonstrates photochromism by using a biimidazole for the basic framework and introducing a bulky substituent into $R_{24}$ and $R_{25}$ of the following general formula (2-1). This molecule is a pale yellow form in a stable state, and demonstrates photochromic properties that cause it to isomerize to a colorless structure as a result of irradiating with light, and further isomerize to its original pale yellow color after having isomerized to a red colored form when allowed to stand while protected from light.

[Chemical Formula 2]

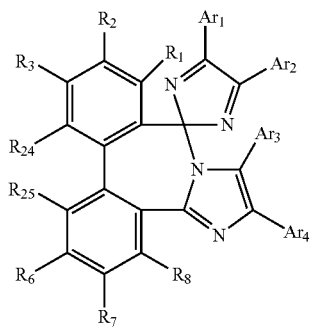

(2-1)

(In the above-mentioned formula, $R_{24}$ and $R_{25}$ respectively and independently represent an alkyl group or an alkyl group having a substituent, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, and $Ar_1$ to $Ar_4$ respectively and independently represent a substituted or unsubstituted aryl group.)

Namely, the present invention is a photochromic material formed of a biimidazole compound represented by the above-mentioned general formula (2-1).

As shown in FIG. 2, the photochromic material of the present invention represented by general formula (2-1) is able to change to an isomer (II-2) as a result of being irradiated with light. The isomer (II-2) changes to an isomer (I-2) and the photochromic material represented by general formula (2-1) due to thermal energy. The isomer (I-2) is normally a colored form that has low transmittance. On the other hand, although the isomer (II-2) is an uncolored form, its transmittance differs from that of the photochromic material represented by general formula (2-1). Thus, according to the photochromic material of the present invention, the color tone of the photochromic material can be adjusted in two stages. Furthermore, in FIG. 2, Δ indicates thermal energy. Furthermore, FIG. 2 shows a drawing in which $R_4$ in FIG. 1 has been replaced with $R_{24}$ and $R_5$ has been replaced with $R_{25}$.

Moreover, the inventors of the present invention discovered a novel compound that demonstrates photochromism by using a biimidazole for the framework and substituting a bulky substituent into $R_4$ and $R_5$ of general formula (3-1).

[Chemical Formula 3]

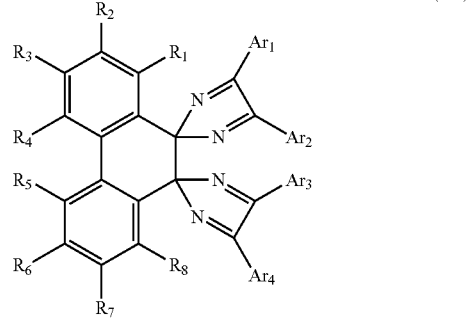

(3-1)

(In the above-mentioned formula, $R_4$ and $R_5$ respectively and independently represent a halogen atom or alkyl group, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, $Ar_1$ to $Ar_4$ respectively and independently represent a substituted or unsubstituted aryl group, $R_4$ may form a condensed, substituted or unsubstituted aryl ring with $R_3$, and $R_5$ may form a condensed, substituted or unsubstituted aryl ring with $R_6$.)

Namely, the present invention is a photochromic material formed of a biimidazole compound represented by the above-mentioned general formula (3-1).

As shown in FIG. 1, the photochromic material of the present invention represented by general formula (3-1) is able to maintain the structure represented by general formula (3-1) as a result of continuing to be irradiated with light. In addition, the photochromic material of the present invention can be changed to the isomer represented by general formula (1-1) by thermal energy as a result of allowing to stand in a state protected from light, thereby lowering transmittance and becoming a colored form. Moreover, the isomer represented by general formula (1-1) is able to change to the isomer (II) due to thermal energy when allowed to stand in a state protected from light. However, among the photochromic materials of the present invention represented by general formula (3-1), although a photochromic material in which $R_4$ forms a condensed, substituted or unsubstituted aryl ring with $R_3$ and $R_5$ forms a condensed, substituted or unsubstituted aryl ring with $R_6$ in general formula (3-1) can normally become the isomer represented by general formula (1-1) as a result of protecting from light, the isomer represented by general formula (1-1) does not become the isomer (II) shown in FIG. 1 even if the isomer represented by general formula (1-1) is further allowed to stand in state protected from light (see FIG. 3).

Effects of the Invention

According to the photochromic material provided by the present invention, the following effects (1), (2) and (3) are obtained.

(1) Color tone changes from a colored form to an uncolored form as a result of irradiating with visible light.

(2) Color tone can be changed from a pale yellow color to an uncolored form by easily increasing transmittance as a result of irradiating with light, and can be subsequently changed to a colored form or returned to the photochromic material of the present invention by lowering transmittance with thermal energy.

(3) Color tone can be easily changed from an uncolored form to a colored form by irradiating with light.

The above-mentioned properties are considered to be able to be applied to all types of applications in which photochromic molecules are used. Specific examples of applications include optical switches, printing materials, recording materials and holographic materials.

Moreover, since the photochromic material of the present invention has a completely different structure from that of conventional molecules demonstrating photochromism, it is also able to provide a new choice when developing devices that utilize photochromism.

Figure 1:
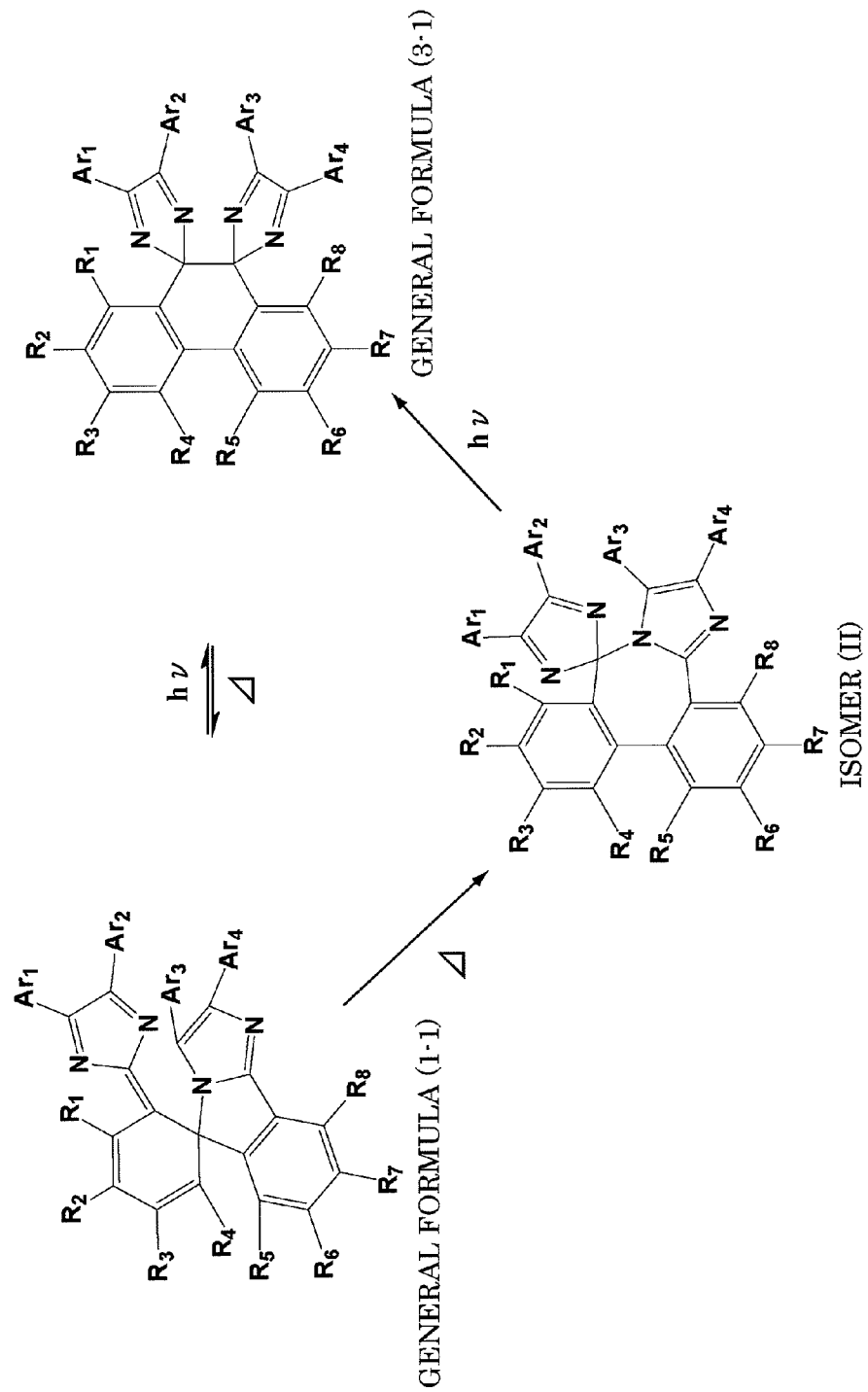
FIG. 1 is a drawing showing structures able to be adopted by the photochromic material of the present invention represented by general formula (1-1) or (3-1) as a result of being irradiated with light or protecting from light.

Hereinafter, embodiments of the present invention will be described.

MODES FOR CARRYING OUT THE INVENTION

<First Embodiment>

First, an explanation is provided of a first embodiment of the present invention.

The first embodiment of the photochromic material of the present invention allows the obtaining of a structure having a spiro-cyclic structure by introducing sterically bulky substituents into both sites $R_4$ and $R_5$ of a biimidazole compound represented by general formula (1-1).

Examples of bulky substituents of both sites $R_4$ and $R_5$ include a halogen atom and an alkyl group. The above-mentioned substituents may be methyl groups, which constitute the smallest alkyl groups. Namely, the photochromic material may be represented by the following general formula (1-2).

[Chemical Formula 4]

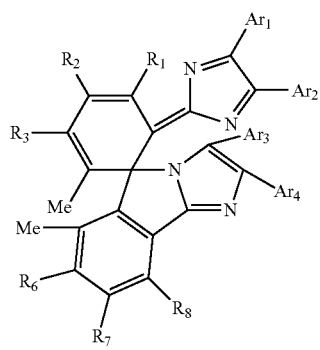

(1-2)

Alternatively, $R_4$ may form a condensed, substituted or unsubstituted aryl ring with $R_3$, and $R_5$ may form a condensed, substituted or unsubstituted aryl ring with $R_6$. Here, the aryl ring is preferably a benzene ring. The photochromic material in this case is represented by the following general formula (1-3):

[Chemical Formula 5]

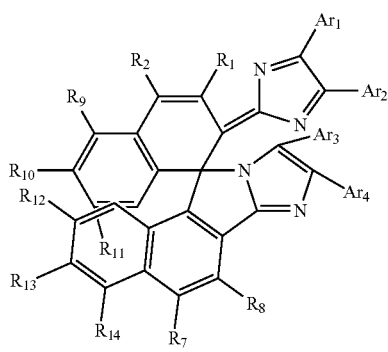

(1-3)

(In the formula, $R_1$ and $R_2$ as well as $R_7$ to $R_{14}$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, and $Ar_1$ to $Ar_4$ respectively and independently represent a substituted or unsubstituted aryl group).

The photochromic material of the present invention is obtained by, for example, reacting a 2,2'-diformylbiphenyl derivative represented by the following general formula (1-4) with diarylethanedione derivatives represented by the following general formulas (1-5) and (1-6) in the presence of a nitrogen compound to obtain an intermediate containing an imidazole ring, followed by oxidizing that intermediate. Here, a 2,2'-diformyl-1,1'-binaphthalene derivative can be used instead of the 2,2'-diformylbiphenyl derivative represented by general formula (1-4). In addition, 2,2'-diformylbiphenyl is not included in the 2,2'-diformylbiphenyl derivative. This is because the photochromic material of the present invention can no longer be obtained if 2,2'-diformylbiphenyl is included. Furthermore, the photochromic material of the present invention is also obtained by reacting different diarylethanedione derivatives with the two formyl groups. The production method of the photochromic material of the present invention may employ any synthesis route provided the structural molecule of the present invention is obtained, and is not limited by the synthesis route.

[Chemical Formula 6]

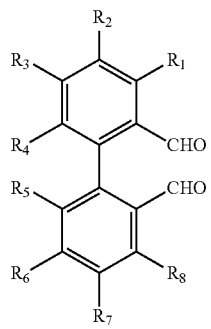

(1-4)

(In the above-mentioned formula, $R_4$ and $R_5$ respectively and independently represent a halogen atom or alkyl group, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, $Ar_1$ to $Ar_4$ respectively and independently represent a substituted or unsubstituted aryl group, $R_4$ may form a condensed, substituted or unsubstituted aryl ring with $R_3$, and $R_5$ may form a condensed, substituted or unsubstituted aryl ring with $R_6$.)

[Chemical Formula 7]

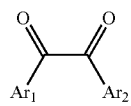

(1-5)

(In the above-mentioned formula, $Ar_1$ and $Ar_2$ respectively and independently represent a substituted or unsubstituted aryl group.)

[Chemical Formula 8]

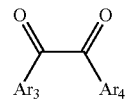

(1-6)

(In the above-mentioned formula, $Ar_3$ and $Ar_4$ respectively and independently represent a substituted or unsubstituted aryl group.)

The 2,2'-diformylbiphenyl derivative used as a raw material for synthesizing the photochromic molecule of the present invention represented by the above-mentioned general formula (1-1) preferably has sterically large substituents at positions 6 and 6'. Examples of such 2,2'-diformylbiphenyl derivatives include, but are not limited to, 6,6'-dimethyl-2,2'-diformylbiphenyl, 6,6'-diethyl-2,2'-diformylbiphenyl, 6,6'-dimethyl-2,2'-di-n-propylbiphenyl, 6,6'-dimethyl-2,2'-diisopropylbiphenyl, 6,6'-dimethyl-2,2'-di-n-butylbiphenyl, 6,6'-dimethyl-2,2'-diisobutylbiphenyl, 6,6'-dimethyl-2,2'-di-tertbutylbiphenyl, 6,6'-ditrifluoromethyl-2,2'-diformylbiphenyl, 4,4'-dihydroxy-6,6'-dimethyl-2,2'-diformylbiphenyl, 4,4'-dimethoxy-6,6'-dimethyl-2,2'-diformylbiphenyl, 4,4'-diacetoxy-6,6'-dimethyl-2,2'-diformylbiphenyl, 4,4'-diamino-6,6'-dimethyl-2,2'-diformylbiphenyl, 4,4'-bis(dimethylamino)-6,6'-dimethyl-2,2'-diformylbiphenyl, 4,4'-difluoro-6,6'-dimethyl-2,2'-diformylbiphenyl, 4,4'-dichloro-6,6'-dimethyl-2,2'-diformylbiphenyl, 4,4'-dibromo-6,6'-dimethyl-2,2'-diformylbiphenyl, 4,4'-diiodo-6,6'-dimethyl-2,2'-diformylbiphenyl, 4,4'-dinitro-6,6'-dimethyl-2,2'-diformylbiphenyl, 4,4'-dicyano-6,6'-dimethyl-2,2'-diformylbiphenyl, 4,4'-dimethoxycarbonyl-6,6'-dimethyl-2,2'-diformylbiphenyl, 3,3',6,6'-tetramethyl-2,2'-diformylbiphenyl, 4,4',6,6'-tetramethyl-2,2'-diformylbiphenyl, 5,5',6,6'-tetramethyl-2,2'-diformylbiphenyl, 6,6'-dichloro-2,2'-diformylbiphenyl, 6,6'-dibromo-2,2'-diformylbiphenyl, 6,6'-diiodo-2,2'-diformylbiphenyl, 4,4',6,6'-tetrachloro-2,2'-diformylbiphenyl, 4,4',6,6'-tetrabromo-2,2'-diformylbiphenyl, 4,4'-difluoro-6,6'-dichloro-2,2'-diformylbiphenyl, 4,4'-difluoro-6,6'-dibromo-2,2'-diformylbiphenyl, 4,4'-difluoro-6,6'-diiodo-2,2'-diformylbiphenyl, 3,3',4,4',5,5'-hexafluoro-6,6'-dibromo-2,2'-diformylbiphenyl, and 5,5'-dimethoxy-4,4',6,6'-tetramethyl-2,2'-diformylbiphenyl.

In addition, examples of 2,2'-diformyl-1,1'-binaphthalene derivatives include, but are not limited to, 2,2'-diformyl-1,1'-binaphthalene, 3,3'-dibromo-2,2'-diformyl-1,1'-binaphthalene, 4,4'-dibromo-2,2'-diformyl-1,1'-binaphthalene, 6,6'-dibromo-2,2'-diformyl-1,1'-binaphthalene, 3,3'-dichloro-2,2'-diformyl-1,1'-binaphthalene, 3,3'-diiodo-2,2'-diformyl-1,1'-binaphthalene, 3,3'-dimethoxymethyl-2,2'-diformyl-1,1'-binaphthalene, 3,3'-diphenyl-2,2'-diformyl-1,1'-binaphthalene, 6,6'-dimethoxycarbonyl-2,2'-diformyl-1,1'-binaphthalene, 4,4'-dicyano-2,2'-diformyl-1,1'-binaphthalene, 7,7'-dihydroxy-2,2'-diformyl-1,1'-binaphthalene, 7,7'-dimethoxy-2,2'-diformyl-1,1'-binaphthalene, 7,7'-bis(metachlorobenzyloxy)-2,2'-diformyl-1,1'-binaphthalene, 6,6'-dibromo-3,3'-dimethoxy-2,2'-diformyl-1,1'-binaphthalene, 3,3'-dimethoxycarbonyl-4,4'-dihydroxy-2,2'-diformyl-1,1'-binaphthalene, 3,3',6,6'-tetraphenyl-2,2'-diformyl-1,1'-binaphthalene, 6,6'-dimethyl-7,7'-dihydroxy-2,2'-diformyl-1,1'-binaphthalene, 6,6'-dimethyl-7,7'-bis(metachlorobenzyloxy)-2,2'-diformyl-1,1'-binaphthalene, 3,3',4,4'-tetrahydroxy-2,2'-diformyl-1,1'-binaphthalene, 3,3'-dimethoxy-4,4'-diamino-2,2'-diformyl-1,1'-binaphthalene, 6,6'-dimethyl-7,7'-dihydroxy-2,2'-diformyl-1,1'-binaphthalene, and 6-methoxycarbonylethyl-2,2'-diformyl-1,1'-binaphthalene.

Examples of diarylethanedione derivatives represented by general formulas (1-5) and (1-6) used as raw materials of the photochromic material of the present invention include, but are not limited to, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 2-iodobenzyl, 3-iodobenzyl, 4-iodobenzyl, 2-hydroxybenzyl, 3-hydroxybenzyl, 4-hydroxybenzyl, 2-methoxybenzyl, 3-methoxybenzyl, 4-methoxybenzyl, 2-ethoxybenzyl, 3-ethoxybenzyl, 4-ethoxybenzyl, 2-phenoxybenzyl, 3-phenoxybenzyl, 4-phenoxybenzyl, 2-acetoxybenzyl, 3-acetoxybenzyl, 4-acetoxybenzyl, 2-methylbenzyl, 3-methylbenzyl, 4-methylbenzyl, 2-carboxybenzyl, 3-carboxybenzyl, 4-carboxybenzyl, 2-(methylcarboxy)benzyl, 3-(methylcarboxy)benzyl, 4-(methylcarboxy)benzyl, 2-(phenylcarboxy)benzyl, 3-(phenylcarboxy)benzyl, 4-(phenylcarboxy)benzyl, 2-nitrobenzyl, 3-nitrobenzyl, 4-nitrobenzyl, 2-cyanobenzyl, 3-cyanobenzyl, 4-cyanobenzyl, 2-methylthiobenzyl, 3-methylthiobenzyl, 4-methylthiobenzyl, 2-phenylthiobenzyl, 3-phenylthiobenzyl, 4-phenylthiobenzyl, 2-phenylacetylenylbenzyl, 3-phenylacetylenylbenzyl, 4-phenylacetylenylbenzyl, 2-styrylbenzyl, 3-styrylbenzyl, 4-styrylbenzyl, 2-phenylmethylbenzyl, 3-phenylmethylbenzyl, 4-phenylmethylbenzyl, 2-aminobenzyl, 3-aminobenzyl, 4-aminobenzyl, 2-dimethylaminobenzyl, 3-dimethylaminobenzyl, 4-dimethylaminobenzyl, 2-bromomethylbenzyl, 3-bromomethylbenzyl, 4-bromomethylbenzyl, 2-methoxymethylbenzyl, 3-methoxymethylbenzyl, 4-methoxymethylbenzyl, 2-(N-methylaminocarbonyl)benzyl, 3-(N-methylaminocarbonyl)benzyl, 4-(N-methylaminocarbonyl)benzyl, 2-(N-phenylaminocarbonyl)benzyl, 3-(N-phenylaminocarbonyl)benzyl, 4-(N-phenylaminocarbonyl)benzyl, 2-trifluoromethylbenzyl, 3-trifluoromethylbenzyl, 4-trifluoromethylbenzyl, 3,4-methylenedioxybenzyl, 3,4-ethylenedioxybenzyl, 3,4-ethylenedithiobenzyl, 2,4-dihydroxybenzyl, 2,4-dimethylbenzyl, 2,3-dimethylbenzyl, 3,4-dimethylbenzyl, 3,4-dimethoxybenzyl, 2,4-dimethoxybenzyl, 2,4-dinitrobenzyl, 2-methyl-3-nitrobenzyl, 2-methoxy-3-nitrobenzyl, 2-chloro-4-methoxybenzyl, 3-chloro-4-aminobenzyl, 2,3-dichlorobenzyl, 3,4-dichlorobenzyl, 2-difluoromethyl-3-methylbenzyl, 3-fluoro-4-bromobenzyl, 3,5-dimethoxybenzyl, 3,5-difluorobenzyl, 3,4,5-trimethoxybenzyl, 4-(2-oxo-phenylacetyl)naphthalene-1,8-dicarboxlyic acid anhydride, 1-(9-oxofluoren-2-yl)-2-phenylethanedione, 1-(4-nitrophenyl)-3-[4-(2-oxo-2-phenylacetyl)phenyl]urea, ethyl-4-methyl-2-{[4-(2-oxo-2-phenylacetyl)phenyl]carbonylamino}-1,3-thiazol-5-carboxylate, N-(2-methoxy-5-methylphenyl)[4-(2-oxo-2-phenylacetyl)phenyl]carboxyamide, N-(2-methoxyethyl)[4-(2-oxo-2-phenylacetyl)phenyl]carboxyamide, 4-chloro-2-methylphenyl-4-(2-oxo-2-phenylacetyl)benzoate, 1-phenyl-2-(2-naphthyl)ethanedione, 1-phenyl-2-(1-naphthyl)ethanedione, 1-phenyl-2-[4-(4-nitrophenoxy)phenyl]ethanedione, carbamoylmethyl-4-(2-oxo-2-phenylacetyl)benzoate, 1-acenaphthen-5-yl-2-phenylethanedione, 2,3,4,5,6-pentachlorobenzyl, benzyl, 2,2'-difluorobenzyl, 3,3'-difluorobenzyl, 4,4'-difluorobenzyl, 2,2'-dichlorobenzyl, 3,3'-dichlorobenzyl, 4,4'-dichlorobenzyl, 2,2'-dibromobenzyl, 3,3'-dibromobenzyl, 4,4'-dibromobenzyl, 2,2'-diiodobenzyl, 3,3'-diiodobenzyl, 4,4'-diiodobenzyl, 2,2'-dihydroxybenzyl, 3,3'-dihydroxybenzyl, 4,4'-dihydroxybenzyl, 2,2'-dimethoxybenzyl, 3,3'-dimethoxybenzyl, 4,4'-dimethoxybenzyl, 2,2'-diethoxybenzyl, 3,3'-diethoxybenzyl, 4,4'-diethoxybenzyl, 2,2'-diphenoxybenzyl, 3,3'-diphenoxybenzyl, 4,4'-diphenoxybenzyl, 2,2'-diacetoxybenzyl, 3,3'-diacetoxybenzyl, 4,4'-diacetoxybenzyl, 2,2'-dimethylbenzyl, 3,3'-dimethylbenzyl, 4,4'-dimethylbenzyl, 2,2'-dicarboxybenzyl, 3,3'-dicarboxybenzyl, 4,4'-dicarboxybenzyl, 2,2'-bis(methylcarboxy)benzyl, 3,3'-bis(methylcarboxy)benzyl, 4,4'-bis(methylcarboxy)benzyl, 2,2'-bis(phenylcarboxy)benzyl, 3,3'-bis(phenylcarboxy)benzyl, 4,4'-bis(phenylcarboxy)benzyl, 2,2'-dinitrobenzyl, 3,3'-dinitrobenzyl, 4,4'-dinitrobenzyl, 2,2'-dicyanobenzyl, 3,3'-dicyanobenzyl, 4,4'-dicyanobenzyl, 2,2'-dimethylthiobenzyl, 3,3'-dimethylthiobenzyl, 4,4'-dimethylthiobenzyl, 2,2'-diphenylthiobenzyl, 3,3'-diphenylthiobenzyl, 4,4'-diphenylthiobenzyl, 2,2'-diphenylacetylenylbenzyl, 3,3'-diphenylacetelenylbenzyl, 4,4'-diphenylacetylenylbenzyl, 2,2'-distyrylbenzyl, 3,3'-distyrylbenzyl, 4,4'-distyrylbenzyl, 2,2'-diphenylmethylbenzyl, 3,3'-diphenylmethylbenzyl, 4,4'-diphenylmethylbenzyl, 2,2'-diaminobenzyl, 3,3'-diaminobenzyl, 4,4'-diaminobenzyl, 2,2'-bis(dimethylamino)benzyl, 3,3'-bis(dimethylamino)benzyl, 4,4'-bis(dimethylamino)benzyl, 2,2'-dibromomethylbenzyl, 3,3'- dibromomethylbenzyl, 4,4'-dibromomethylbenzyl, 2,2'-dimethoxymethylbenzyl, 3,3'-dimethoxymethylbenzyl, 4,4'-dimethoxymethylbenzyl, 2,2'-bis(N-methylaminocarbonyl)benzyl, 3,3'-bis(N-methylaminocarbonyl)benzyl, 4,4'-bis(N-methylaminocarbonyl)benzyl, 2,2'-bis(N-phenylaminocarbonyl)benzyl, 3,3'-bis(N-phenylaminocarbonyl)benzyl, 4,4'-bis(N-phenylaminocarbonyl)benzyl, 2,2'-bis(trifluoromethyl)benzyl, 3,3'-bis(trifluoromethyl)benzyl, 4,4'-bis(trifluoromethyl)benzyl, 3,4,3',4'-dimethylenedioxybenzyl, 3,4,3',4'-diethylenedioxybenzyl, 3,4,3',4'-diethylenedithiobenzyl, 2,2',4,4'-tetramethylbenzyl, 3,3',4,4'-tetramethoxybenzyl, 2,2',4,4'-tetramethoxybenzyl, 2,2',4,4'-tetranitrobenzyl, 2,2'-dimethyl-3,3'-dinitrobenzyl, 2,2'-dimethoxy-3,3'-dinitrobenzyl, 2,2'-dichloro-4,4'-dimethoxybenzyl, 3,3'-dichloro-4,4'-diaminobenzyl, 2,2',3,3'-tetrachlorobenzyl, 3,3',4,4'-tetrachlorobenzyl, 2,2'-bis(difluoromethyl)-3,3'-dimethylbenzyl, 3,3'-difluoro-4,4'-dibromobenzyl, 3,3'5,5'-tetramethoxybenzyl, 3,3',5,5'-tetrafluorobenzyl, 3,3',4,4',5,5'-hexamethoxybenzyl, 4,4'-bis (3-methyl-3-hydroxy-1-butynyl)benzyl, 4,4'-diphenylbenzyl, 4,4'-bis(N-morpholinyl)benzyl, 1,2-bis(2,3,6,7-tetrahydro-1H,5H-pyrido[3,2,1-ij]quinolin-9-yl) ethanedione, 3,3'-dinitro-4,4'-dichlorobenzyl, 3,3'-dinitro-4,4'-dimethoxybenzyl, 3,3'-dinitro-4,4'-dibromobenzyl, 4-methyl-4'-chlorobenzyl, 2-chloro-3',4'-dimethoxybenzyl, 2,4'-dibromobenzyl, and 2,3,4,5,6-pentachloro-2',3',4',5',6'-pentafluorobenzyl.

Although the temperature for reacting the 2,2'-diformylbiphenyl derivative represented by general formula (1-4) and the diarylethanedione derivatives represented by general formulas (1-5) and (1-6) cannot be uniformly defined since it varies according to the presence or absence of catalyst and the type of catalyst used, in the case of, for example, using acetic acid for the solvent without using a catalyst, the reaction temperature is normally 80° C. to 120° C. and preferably 100° C. to 120° C. In addition, in the case of using, for example, ZrCl$_4$ or iodine as catalyst, the reaction temperature can be 20° C. to 75° C. in the presence of the catalyst.

Although the reaction time can also not be uniformly defined since it varies according to the presence or absence of catalyst and the type of catalyst used, in the case of using, for example, acetic acid for the solvent and not using a catalyst, the reaction temperature is 4 hours to 32 hours and preferably 12 hours to 24 hours. In addition, in the case of using, for example, ZrCl$_4$ or iodine as catalyst, the reaction time can be 1 hour to 10 hours in the presence of the catalyst.

Although examples of the above-mentioned nitrogen compound include ammonium acetate and ammonia, ammonia acetate is particularly preferable since it less likely to volatilize during heating.

There are no particular limitations on the solvent of the above-mentioned reaction and any solvent can be used provided it is able to dissolve the raw material. Preferable examples of the solvent include polar solvents such as acetic acid or acetonitrile.

The intermediate oxidation reaction can be carried out by preparing a solution by dissolving the intermediate in a solvent, for example, followed by adding an oxidizing agent to this solution.

There are no particular limitations on the solvent and any solvent can be used provided it is able to dissolve the intermediate. Examples of such solvents include benzene and methylene chloride.

There are no particular limitations on the oxidizing agent and any oxidizing agent can be used provided it allows the obtaining of a photochromic material represented by general formula (1-1) by oxidizing the intermediate. Although examples of such oxidizing agents include potassium ferricyanide and lead oxide, potassium ferricyanide is particularly preferable. This is because potassium ferricyanide has higher reactivity.

Furthermore, a base can be further added to the above-mentioned solution in addition to the oxidizing agent. Examples of such bases include potassium hydroxide.

The oxidation reaction is preferably carried out in an inert gas atmosphere and under protection from light. The reaction is carried out in an inert gas atmosphere in order to inhibit reaction with oxygen. Nitrogen, for example, can be used for the inert gas. The oxidation reaction is preferably carried out under protection from light in order to prevent the resulting photochromic material from being changed from a colored form to an uncolored form by light.

<Second Embodiment>

The following provides an explanation of a second embodiment of the present invention.

A second embodiment of the photochromic material of the present invention allows the obtaining of a structure having a spiro-cyclic structure by introducing sterically bulky substituents into both sites $R_{24}$ and $R_{25}$ of a biimidazole compound represented by general formula (2-1).

Examples of bulky substituents introduced at both sites R24 and R25 include alkyl groups and alkyl groups having a substituent. Examples of substituents include a halogen atom, hydroxyl group, alkoxyl group, amino group and alkylamino group. The bulky substituents at both sites $R_4$ and $R_5$ may be methyl groups, which constitute the smallest alkyl groups. Namely, the photochromic material may be represented by the following general formula (2-2).

[Chemical Formula 9]

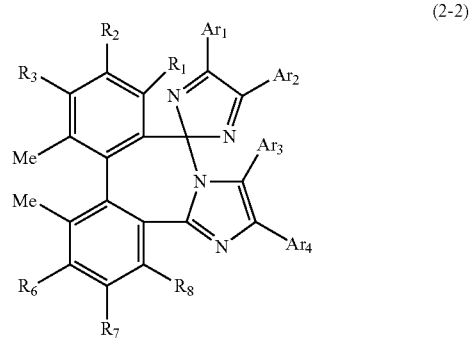

(2-2)

Figure 2:
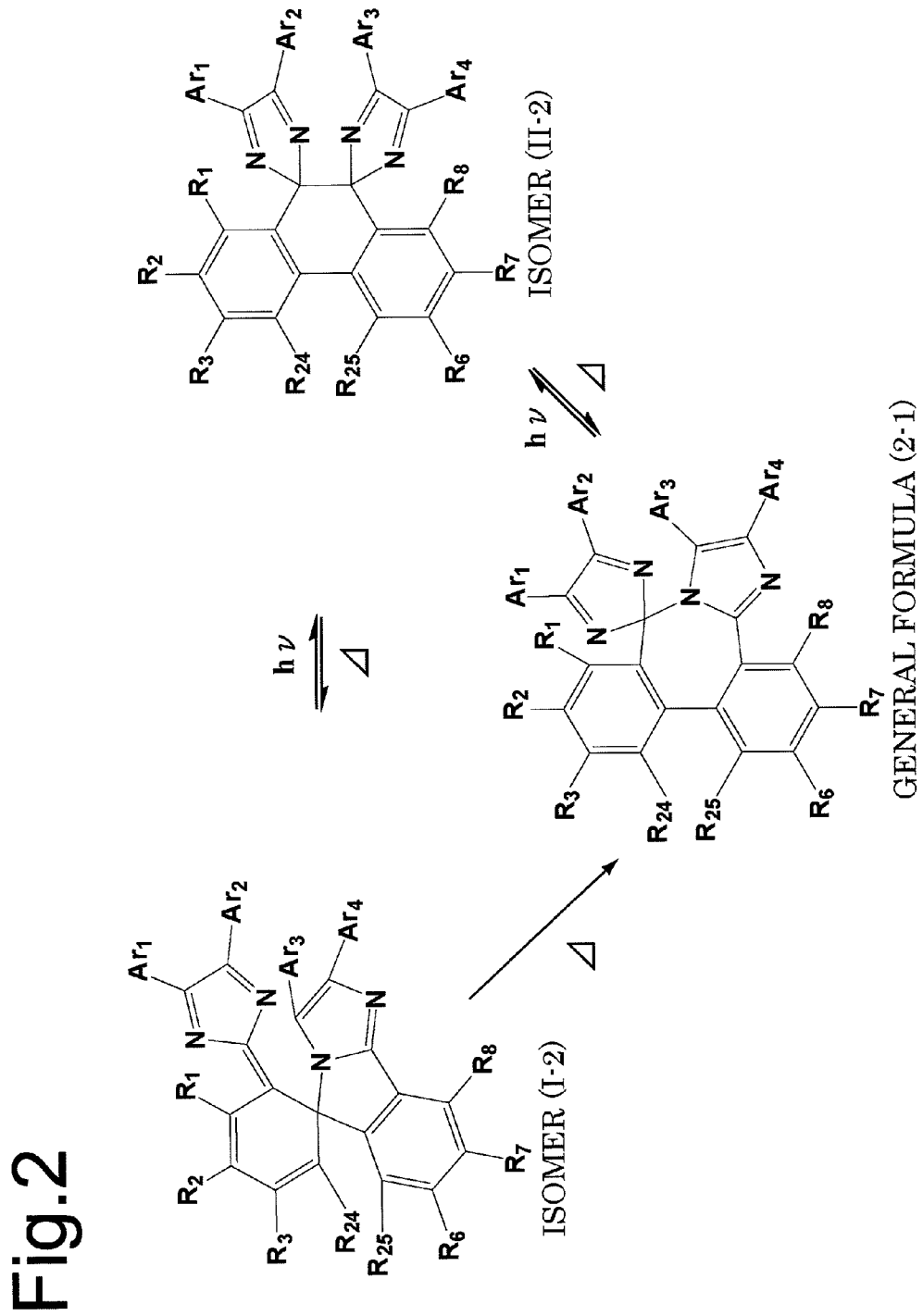
FIG. 2 is a drawing showing structures able to be adopted by the photochromic material of the present invention represented by general formula (2-1) as a result of being irradiated with light or protecting from light.

The photochromic material of the present invention is obtained by producing an isomer (II-2) shown in FIG. 2 by reacting a 2,2'-diformylbiphenyl derivative represented by the following general formula (2-3) with the diarylethanedione derivatives represented by the above-mentioned general formulas (1-5) and (1-6) in the presence of a nitrogen compound to obtain an intermediate containing an imidazole ring, followed by oxidizing the intermediate, and then allowing the isomer (II-2) to stand while protected from light. In addition, 2,2'-diformylphenyl is not included in the 2,2'-diformylphenyl derivative. This is because the photochromic material of the present invention can no longer be obtained if 2,2'-diformylbiphenyl is included. Furthermore, the photochromic material of the present invention is also obtained by reacting different diarylethanedione derivatives with the two formyl groups. The production method of the photochromic material of the present invention may employ any synthesis route provided the structural molecule of the present invention is obtained, and is not limited by the synthesis route.

[Chemical Formula 10]

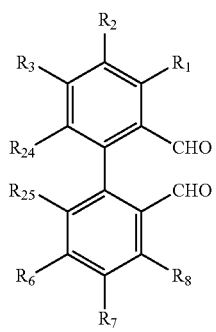

(2-3)

(In the above-mentioned formula, $R_{24}$ and $R_{25}$ respectively and independently represent an alkyl group or an alkyl group having a substituent, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, and $Ar_1$ to $Ar_4$ respectively and independently represent a substituted or unsubstituted aryl group.)

The 2,2'-diformylphenyl derivative used for the synthesis raw material of the photochromic material of the present invention represented by the above-mentioned general formula (2-1) preferably has sterically large substituents at positions 6 and 6'. The same compounds as those of the first embodiment can be used for such 2,2'-diformylbiphenyl derivatives with the exception of 6,6'-dichloro-2,2'-diformylbiphenyl, 6,6'-dibromo-2,2'-di formylbiphenyl, 6,6'-diiodo-2,2'-diformylbiphenyl, 4,4', 6,6'-tetrachloro-2,2'-diformylbiphenyl, 4,4',6,6'-tetrabromo-2,2'-diformylbiphenyl, 4,4'-difluoro-6,6'-dichloro-2,2'-diformylbiphenyl, 4,4'-difluoro-6,6'-dibromo-2,2'-diformylbiphenyl, 4,4'-difluoro-6,6'-diiodo-2,2'-diformylbiphenyl, and 3,3', 4,4',5,5'-hexafluoro-6,6'-dibromo-2,2'-diformylbiphenyl.

Examples of diarylethanedione derivatives represented by general formulas (1-5) and (1-6) used as raw materials of the photochromic material of the present invention include those listed as examples in the first embodiment, as well as 1,2-bis(2-naphthyl)ethanedione, 1,2-bis(1-naphthyl)ethanedione and 1,2-bis(2-(6-methoxyphenyl)ethanedione.

The temperature for reacting the 2,2'-diformylbiphenyl derivative represented by general formula (2-3) and the diarylethanedione derivatives represented by general formulas (1-5) and (1-6) is the same as in the first embodiment.

The reaction time, nitrogen compound, solvent of the above-mentioned reaction, oxidation reaction of the above-mentioned intermediate and solvent used in the oxidation reaction of the above-mentioned intermediate are the same as in the first embodiment.

There are no particular limitations on the oxidizing agent and any oxidizing agent can be used provided it allows the obtaining of the isomer (II-2) by oxidizing the intermediate. Although examples of such oxidizing agents include potassium ferricyanide and lead oxide, potassium ferricyanide is particularly preferable. This is because potassium ferricyanide has higher reactivity.

Furthermore, a base is further added to the above-mentioned solution in addition to the oxidizing agent. Examples of such bases include potassium hydroxide.

The oxidation reaction is preferably carried out in an inert gas atmosphere and under protection from light. The reaction is carried out in an inert gas atmosphere in order to inhibit reaction with oxygen. Nitrogen, for example, can be used for the inert gas. The oxidation reaction is preferably carried out under protection from light in order to prevent an isomerization reaction.

The isomer (II-2) changes to the photochromic material of the present invention represented by general formula (2-1) when allowed to stand under protection from light. Consequently, this isomer (II-2) is allowed to stand under protection from light in order to obtain the photochromic material of the present invention. Furthermore, since the three types of compounds shown in FIG. 2 cause thermal isomerization reactions, the photochromic material represented by general formula (2-1) does not necessarily only yield the isomer (II-2) as a result of being irradiated with light, but rather can also be in the form of a mixture with isomer (I-2) and the photochromic material represented by general formula (2-1).

The temperature while the above-mentioned isomer (II-2) is protected from light is normally 10° C. to 50° C. and preferably 25° C. to 40° C.

The time during which the above-mentioned isomer (II-2) is allowed to stand under protection from light is normally 50 hours to 100 hours and preferably 70 hours to 80 hours.

<Third Embodiment>

The following provides an explanation of a third embodiment of the present invention.

A third embodiment of the photochromic material of the present invention represented by general formula (3-1) allows the obtaining of a structure having a spiro-cyclic structure by introducing sterically bulky substituents into both sites $R_4$ and $R_5$ of a biimidazole compound represented by general formula (3-1).

Examples of bulky substituents at both sites $R_4$ and $R_5$ include halogen atoms and an alkyl groups. In this case, the photochromic material represented by general formula (3-1) can maintain a structure represented by general formula (3-1) by continuous irradiation with light, and as shown in FIG. 1, can change to the isomer represented by general formula (1-1) and the isomer (II) by being protected from light. Normally, the isomer represented by general formula (1-1) is in a colored form and has low transmittance. In addition, although the isomer (II) is also in a colored form, its transmittance differs from that of the isomer represented by general formula (1-1). The photochromic material represented by general formula (3-1) is an uncolored form, and has transmittance that differs from the isomer represented by general formula (1-1) and the isomer (II). Thus, color tone of the photochromic material can be adjusted in two stages.

The above-mentioned substituents may also be methyl groups, which constitute the smallest alkyl groups. Namely, the photochromic material may be represented with the following general formula (3-2).

[Chemical Formula 11]

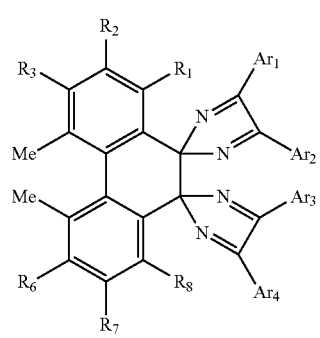

(3-2)

In general formula (3-1), $R_4$ may form a condensed, substituted or unsubstituted aryl ring with $R_3$, and $R_5$ may form a condensed, substituted or unsubstituted aryl ring with $R_6$. Here, the aryl ring is preferably a benzene ring. The photochromic material in this case is represented by the following general formula (3-3). Although the photochromic material represented by general formula (3-3) normally yields the isomer represented by general formula (1-1) when in a state protected from light, it does not yield the isomer (II) shown in FIG. 1 even if further protected from light.

[Chemical Formula 12]

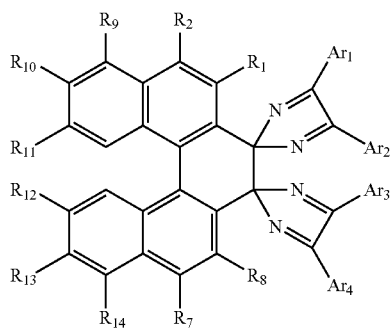

(3-3)

(In the above-mentioned formula, $R_1$ and $R_2$ as well as $R_7$ to $R_{14}$ respectively and independently represent a hydrogen atom, halogen atom, alkyl group, fluoroalkyl group, hydroxyl group, alkoxyl group, amino group, alkylamino group, carbonyl group, alkylcarbonyl group, nitro group, cyano group or aryl group, and $Ar_1$ to $Ar_4$ respectively and independently represent a substituted or unsubstituted aryl group.)

Figure 3:
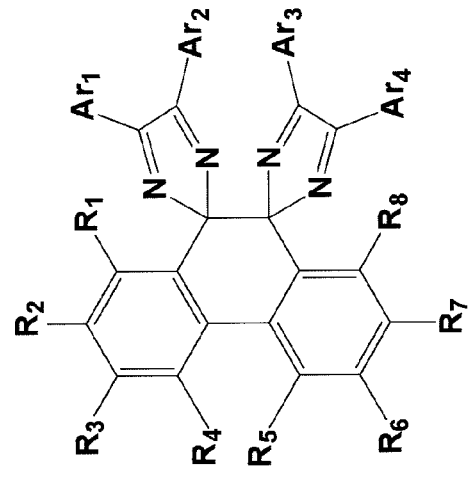
FIG. 3 is a drawing showing structures able to be adopted by a photochromic material in which $R_4$ forms a condensed, substituted or unsubstituted aryl ring with $R_3$ and $R_5$ forms a condensed, substituted or unsubstituted aryl ring with $R_6$ in general formula (3-1) as a result of being irradiated with light or protecting from light.
Figure 3:
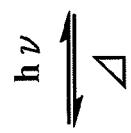

The photochromic material of the present invention is obtained by reacting the 2,2'-diformylbiphenyl derivative represented by the above-mentioned general formula (1-4) with the diarylethanedione derivatives represented by the above-mentioned general formulas (1-5) and (1-6) in the presence of a nitrogen compound to obtain an intermediate containing an imidazole ring, followed by oxidizing that intermediate to obtain the isomer represented by general formula (1-1) shown in FIG. 3 and irradiating this isomer represented by general formula (1-1) with visible light. Here, a 2,2'-diformyl-1,1'-binaphthalene derivative can be used instead of the 2,2'-diformylbiphenyl derivative represented by general formula (1-4). In addition, 2,2'-diformylbiphenyl is not included in the 2,2'-diformylbiphenyl derivative. This is because the isomer represented by general formula (1-1) is not obtained if 2,2'-diformylbiphenyl is included, and as a result thereof, the photochromic material of the present invention can no longer be obtained. Furthermore, the photochromic material of the present invention is also obtained by reacting different diarylethanedione derivatives with the two formyl groups. The production method of the photochromic material of the present invention may employ any synthesis route provided the structural molecule of the present invention is obtained, and is not limited by the synthesis route.

The 2,2'-diformylphenyl derivative used for the synthesis raw material of the photochromic material of the present invention represented by the above-mentioned general formula (3-1) preferably has sterically large substituents at positions 6 and 6' in the same manner as the first embodiment, and the same compounds as those of the first embodiment can be used for such 2,2'-diformylbiphenyl derivatives.

In addition, the same compounds as those of the first embodiment can be used for the 2,2'-diformyl-1,1'-binaphthalene derivative.

Examples of diarylethanedione derivatives represented by general formulas (1-5) and (1-6) used as raw materials of the photochromic material of the present invention include those listed as examples in the first embodiment.

The temperature for reacting the 2,2'-diformylbiphenyl derivative represented by general formula (1-4) and the diarylethanedione derivatives represented by general formulas (1-5) and (1-6) is the same as in the first embodiment.

The reaction time, the above-mentioned nitrogen compound, solvent of the above-mentioned reaction, oxidation reaction of the intermediate and solvent used in the oxidation reaction of the intermediate are the same as in the first embodiment.

There are no particular limitations on the oxidizing agent and any oxidizing agent can be used provided it allows the obtaining of the isomer represented by general formula (1-1) by oxidizing the intermediate. Although examples of such oxidizing agents include potassium ferricyanide and lead oxide, potassium ferricyanide is particularly preferable. This is because potassium ferricyanide has higher reactivity.

Furthermore, a base is further added to the above-mentioned solution in addition to the oxidizing agent. Examples of such bases that can be used include potassium hydroxide.

The oxidation reaction is preferably carried out in an inert gas atmosphere and under protection from light. The reaction is carried out in an inert gas atmosphere in order to inhibit reaction with oxygen. Nitrogen, for example, can be used for the inert gas. The oxidation reaction is preferably carried out under protection from light in order to prevent the isomer represented by general formula (1-1) from being changed from a colored form to an uncolored form by visible light.

Light irradiated onto the isomer represented by general formula (1-1) is light of a wavelength region that includes the wavelength of maximum absorbance in the wavelength region of visible light for the isomer represented by general formula (1-1). Although varying according to intensity of the light, the duration of irradiation with light is normally 10 seconds to 600 seconds and preferably 30 seconds to 300 seconds.

The temperature during irradiation with light is preferably 30° C. or lower and more preferably to 0° C. or lower. If the temperature during irradiation with light is 30° C. or lower, in comparison with the case in which this temperature exceeds 30° C., the efficiency at which the photochromic material of the present invention is produced from the isomer represented by general formula (1-1) is further improved. However, the temperature during irradiation with light is preferably higher than the melting point of the above-mentioned solvent. Namely, irradiation with light is preferably carried out in a state in which the above-mentioned solvent is not a solid.

Furthermore, since the two types of compounds shown in FIG. 3 cause thermal isomerization reactions, the photochromic material represented by general formula (3-1) is not necessarily present alone, but rather can also be in the form of a mixture with the isomer represented by general formula (1-1). More specifically, although the photochromic material represented by general formula (3-1) is formed when the isomer represented by general formula (1-1) is irradiated with light, since a reaction that returns this photochromic material to the structure when irradiated with light, or in other words, to the isomer represented by general formula (1-1), proceeds in the form of a thermal reaction, the isomer represented by general formula (1-1) and the photochromic material represented by general formula (3-1) can be present in the form of a mixture. Similarly, since the three types of compounds shown in FIG. 1 cause a thermal isomerization reaction, the photochromic material represented by general formula (3-1) is not necessarily present alone, but rather can be in the form of a mixture with the isomer represented by general formula (1-1) and the isomer (II).

EXAMPLES

Although the following provides a more specific explanation of the present invention through examples thereof, the present invention is not limited to the following examples.

First, a specific explanation is provided of examples corresponding to the first embodiment of the present invention.

Commercially available reagents (manufactured by Tokyo Chemical Industry Co., Ltd.) were used for the benzyl, 4,4'-dimethoxybenzyl, 4,4'-bis(dimethylamino)benzyl, 4,4'-dibromobenzyl, ammonium acetate, acetic acid, potassium ferricyanide and potassium hydroxide used in the following Synthesis Examples 1-1 to 1-6, 2-1 and 3-1 to 3-5. In addition, measurements by NMR were carried out at 25° C. unless specifically indicated otherwise.

Synthesis Example 1-1

100 mg of 6,6'-dimethyl-2,2'-diformylbiphenyl, 270 mg of 4,4'-dimethoxybenzyl, 960 mg of ammonium acetate and 4.0 ml of acetic acid were mixed, and after allowing to react by heating and stirring for 16 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 273 mg of an intermediate (1-I). Formation of the intermediate (1-I) was confirmed by NMR analysis. Furthermore, the results of NMR analysis were as indicated below.

1H-NMR (500 MHz, CDCl$_3$): δ 8.92 (2H,s), 8.38 (2H, d), 7.53 (2H, t), 7.46 (4H, d), 7.40 (2H, d), 6.94 (4H, d), 6.80 (4H, d), 6.75 (4H, d), 3.78 (12H,s), 1.99 (6H,s)

[Chemical Formula 13]

Intermediate (1-I)

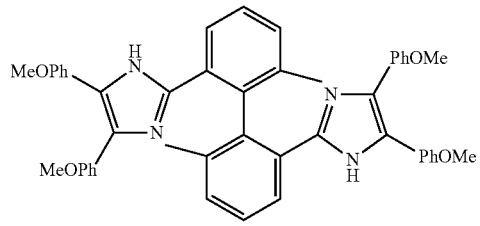

120 mg of the above-mentioned intermediate (1-I) were dissolved in 25 ml of benzene followed by the addition of a solution obtained by dissolving 4.1 g of potassium ferricyanide and 1.8 g of potassium hydroxide in 30 ml of water in the presence of nitrogen and under protection from light, and after allowing to react by stirring for 2 hours at room temperature, the aqueous layer was separated and extracted with benzene, and recrystallization was carried out by concentrating the solvent to obtain 102 mg of a mixture containing 24 mg of Compound [1-1] composed of a reverse photochromic molecule. The formation of Compound [1-1] was confirmed by NMR analysis. Furthermore, although NMR analysis was carried out on the mixture and results for NMR analysis of Compound [1-1] alone were not obtained, since the results indicated the characteristic peaks of a methoxy group and methyl group and the mixture demonstrated photochromic properties, Compound [1-1] represented with the following structural formula was thought to be clearly contained in the mixture.

[Chemical Formula 14]

Compound [1-1]

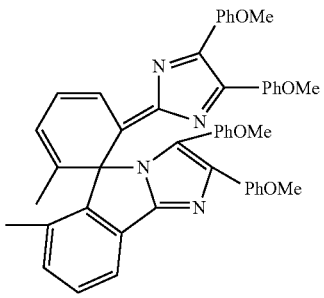

Synthesis Example 1-2

100 mg of 2,2'-diformyl-1,1'-binaphthalene, 183 mg of 4,4'-dimethoxybenzyl, 750 mg of ammonium acetate and 4.0 ml of acetic acid were mixed, and after allowing to react by heating and stirring for 14 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 158 mg of an intermediate (1-II). Formation of the intermediate (1-II) was confirmed by NMR analysis. Furthermore, the results of NMR analysis were as indicated below.

1H-NMR (500 MHz, CDCl$_3$): δ 8.78 (2H, d), 8.45 (2H,s), 8.19 (2H, d), 8.02 (2H, d), 7.55-7.51 (2H, m), 7.42 (4H, d), 7.32-7.30 (4H, m), 6.78 (4H, d), 6.69-6.64 (8H, m), 3.77 (12H,s)

[Chemical Formula 15]

Intermediate (1-II)

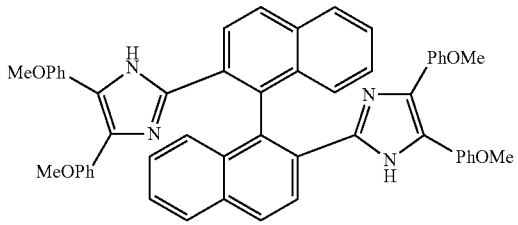

84 mg of the above-mentioned intermediate (1-II) were dissolved in 25 ml of benzene followed by the addition of a solution obtained by dissolving 2.5 g of potassium ferricyanide and 1.1 g of potassium hydroxide in 20 ml of water in the presence of nitrogen and under protection from light, and after allowing to react by stirring for 2 hours at room temperature, the aqueous layer was separated and extracted with benzene, and recrystallization was carried out by concentrating the solvent to obtain 79 mg of Compound [1-2] composed of a reverse photochromic molecule. The formation of Compound [1-2] was confirmed by NMR analysis and X-ray crystal structure analysis. Furthermore, the results of NMR analysis were as indicated below.

1H-NMR (500 MHz, CDCl$_3$): δ 8.24 (1H, d), 7.92 (1H, d), 7.90 (1H, d), 7.77 (1H, d), 7.50 (2H, d), 7.47-7.42 (5H, m), 7.30-7.20 (4H, m), 7.09-7.05 (1H, m), 6.93 (1H, d), 6.89 (1H, d), 6.85 (2H, d), 6.80 (2H, d), 6.73 (2H, d), 6.54 (2H, d), 6.44 (2H, d), 3.82 (3H,s), 3.81 (3H,s), 3.73 (3H,s), 3.73 (3H,s)

[Chemical Formula 16]

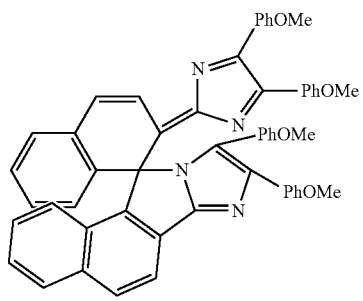

Compound [1-2]

Synthesis Example 1-3

100 mg of 2,2'-diformyl-1,1'-binaphthalene, 149 mg of benzyl, 750 mg of ammonium acetate and 4.0 ml of acetic acid were mixed, and after allowing to react by heating and stirring for 14 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 162 mg of an intermediate (1-III). Formation of the intermediate (1-III) was confirmed by NMR analysis. Furthermore, the results of NMR analysis were as indicated below.

1H-NMR (500 MHz, CDCl$_3$): δ 8.76 (2H, d), 8.69 (2H,s), 8.20 (2H, d), 8.04 (2H, d), 7.56-7.51 (2H, m), 7.51-7.49 (4H, m), 7.33-7.31 (4H, m), 7.24-7.14 (12H, m), 6.75-6.73 (4H, m)

[Chemical Formula 17]

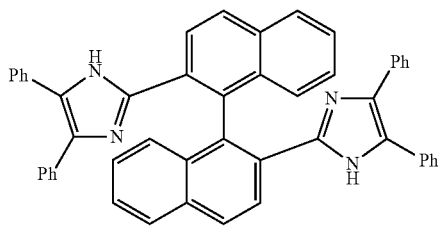

Intermediate (1-III)

87 mg of the above-mentioned intermediate (1-III) were dissolved in 25 ml of benzene followed by the addition of a solution obtained by dissolving 2.9 g of potassium ferricyanide and 1.3 g of potassium hydroxide in 20 ml of water in the presence of nitrogen and under protection from light, and after allowing to react by stirring for 2 hours at room temperature, the aqueous layer was separated and extracted with benzene, and recrystallization was carried out by concentrating the solvent to obtain 75 mg of Compound [1-3] composed of a reverse photochromic molecule. The formation of Compound [1-3] was confirmed by NMR analysis. Furthermore, the results of NMR analysis were as indicated below.

1H-NMR (500 MHz, CDCl$_3$): δ 8.26 (1H, d), 7.93 (2H, d), 7.80 (1H, d), 7.57 (2H, d), 7.47 (2H, d), 7.47 (2H, d), 7.44 (3H, d), 7.40 (1H, d), 7.35-7.31 (4H, m), 7.30-7.21 (3H, m), 7.19-7.15 (3H, m), 7.13-7.07 (2H, m), 7.01 (2H, t), 6.98 (1H, d), 6.94 (1H, d), 6.55 (2H, d)

[Chemical Formula 18]

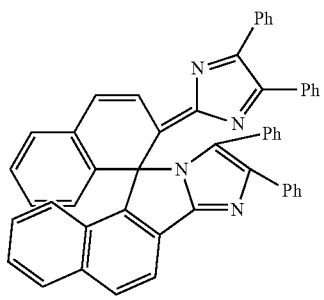

Compound [1-3]

Synthesis Example 1-4

100 mg of 2,2'-diformyl-1,1'-binaphthalene, 210 mg of 4,4'-bis(dimethylamino)benzyl, 750 mg of ammonium acetate and 4.0 ml of acetic acid were mixed, and after allowing to react by heating and stirring for 18 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 114 mg of an intermediate (1-IV). Formation of the intermediate (1-IV) was confirmed by NMR analysis. Furthermore, the results of NMR analysis were as indicated below.

1H-NMR (500 MHz, CDCl$_3$): δ 8.84 (2H,br.s), 8.28 (2H, br.s), 8.18 (2H, d), 8.00 (2H, d), 7.51-7.48 (2H, m), 7.43 (4H,br.s), 7.30-7.28 (4H, m), 6.63 (8H,br.s), 6.49 (4H,br.s), 2.91 (24H,s)

[Chemical Formula 19]

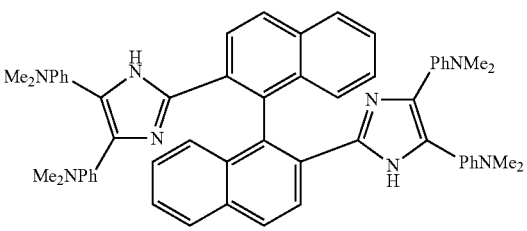

Intermediate (1-IV)

80 mg of the above-mentioned intermediate (1-IV) were dissolved in 25 ml of benzene followed by the addition of a solution obtained by dissolving 2.3 g of potassium ferricyanide and 1.0 g of potassium hydroxide in 20 ml of water in the presence of nitrogen and under protection from light, and after allowing to react by stirring for 2 hours at room temperature, the aqueous layer was separated and extracted with benzene, and a solid was precipitated by concentrating the solvent. The precipitated solid was then recrystallized by dissolving in ethanol to obtain 59 mg of Compound [1-4] composed of a reverse photochromic molecule. The formation of Compound [1-4] was confirmed by NMR analysis. Furthermore, the results of NMR analysis were as indicated below.

1H-NMR (500 MHz, CDCl$_3$): δ 8.23 (1H, d), 7.91 (1H, d), 7.86 (1H, d), 7.74 (1H, d), 7.52-7.50 (3H, m), 7.47 (4H, d), 7.23 (1H, t), 7.19-7.17 (3H, m), 7.02-6.98 (1H, m), 6.89 (1H, d), 6.76 (1H, d), 6.62 (2H, d), 6.59-6.56 (4H, m), 6.40 (2H, d), 6.33 (2H, d), 3.00 (6H,s), 2.99 (6H,s), 2.87 (6H,s), 2.86 (6H,s)

[Chemical Formula 20]

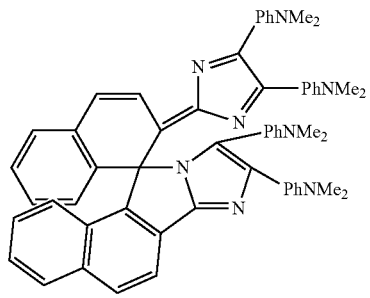

Compound [1-4]

Synthesis Example 1-5

100 mg of 2,2'-diformyl-1,1'-binaphthalene, 261 mg of 4,4'-dibromobenzyl, 750 mg of ammonium acetate and 4.0 ml of acetic acid were mixed, and after allowing to react by heating and stirring for 18 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 249 mg of an intermediate (1-V). Formation of the intermediate (1-V) was confirmed by NMR analysis. Furthermore, the results of NMR analysis were as indicated below.

1H-NMR (500 MHz, CDCl$_3$): δ 8.82 (2H,s), 8.62 (2H, d), 8.19 (2H, d), 8.04 (2H, d), 7.84-7.82 (4H, m), 7.69-7.67 (4H, m), 7.56 (2H, t), 7.35-7.29 (8H, m), 6.61 (4H, d)

[Chemical Formula 21]

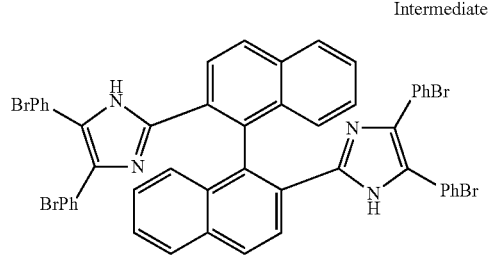

Intermediate (1-V)

80 mg of the above-mentioned intermediate (1-V) were dissolved in 10 ml of benzene followed by the addition of a solution obtained by dissolving 2.0 g of potassium ferricyanide and 0.90 g of potassium hydroxide in 15 ml of water in the presence of nitrogen and under protection from light, and after allowing to react by stirring for 2 hours at room temperature, the aqueous layer was separated and extracted with benzene, and a solid was precipitated by concentrating the solvent. The precipitated solid was then recrystallized by dissolving in ethanol to obtain 22 mg of Compound [1-5] composed of a reverse photochromic molecule. The formation of Compound [1-5] was confirmed by NMR analysis. Furthermore, the results of NMR analysis were as indicated below.

b 1H-NMR (500 MHz, CDCl$_3$): δ 8.21 (1H, d), 7.95 (2H, d), 7.83 (1H, d), 7.49 (2H, d), 7.43 (2H, d), 7.40-7.29 (12H, m), 7.23 (2H, d), 7.16 (2H, d), 7.08 (1H, d), 6.96 (1H, d), 6.36 (2H, d)

[Chemical Formula 22]

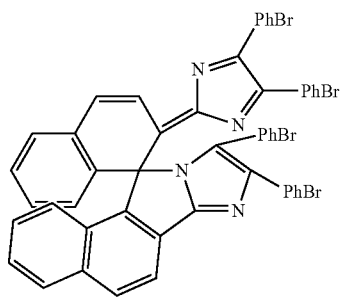

Compound [1-5]

Synthesis Example 1-6

50 mg of 2,2'-diformylbiphenyl, 142 mg of 4,4'-dimethoxybenzyl, 550 mg of ammonium acetate and 3.0 ml of acetic acid were mixed, and after allowing to react by heating and stirring for 24 hours in an oil bath at 110° C., 6.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 136 mg of an intermediate (1-VI). Formation of the intermediate (1-VI) was confirmed by NMR analysis. Furthermore, the results of NMR analysis were as indicated below.

1H-NMR (500 MHz, CDCl$_3$): δ 9.37 (2H,s), 8.31 (2H, d), 7.56 (2H, t), 7.48-7.38 (8H, m), 7.29 (2H, d), 7.00 (2H,br.s), 6.77 (8H, d), 3.78 (12H,s)

[Chemical Formula 23]

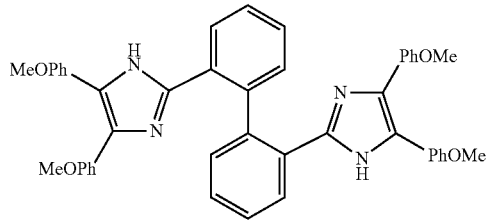

Intermediate (1-VI)

89 mg of the above-mentioned intermediate (1-VI) were dissolved in 35 ml of benzene followed by the addition of a solution obtained by dissolving 3.2 g of potassium ferricyanide and 1.4 g of potassium hydroxide in 25 ml of water in the presence of nitrogen and under protection from light, and after allowing to react by stirring for 2 hours at room temperature, the aqueous layer was separated and extracted with benzene, and a solid was precipitated by concentrating the solvent. Although the precipitated solid was then recrystallized by dissolving in ethanol, 86 mg of Compound [1-6] were obtained that did not demonstrate photochromism. The formation of Compound [1-6] was confirmed by NMR analysis and mass spectroscopy. Furthermore, the results of NMR analysis were as indicated below.

1H-NMR (500 MHz, CDCl$_3$): δ 8.06 (2H, d), 7.45 (2H, t), 7.42 (8H, d), 7.19 (2H, t), 6.99 (2H, d), 6.79 (8H, d), 3.80 (12H,s),

FD-MS: m/z=708 (M$^+$)

[Chemical Formula 24]

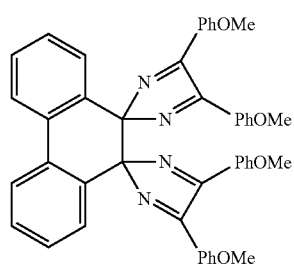

Compound [1-6]

Example 1-1

Figure 4:
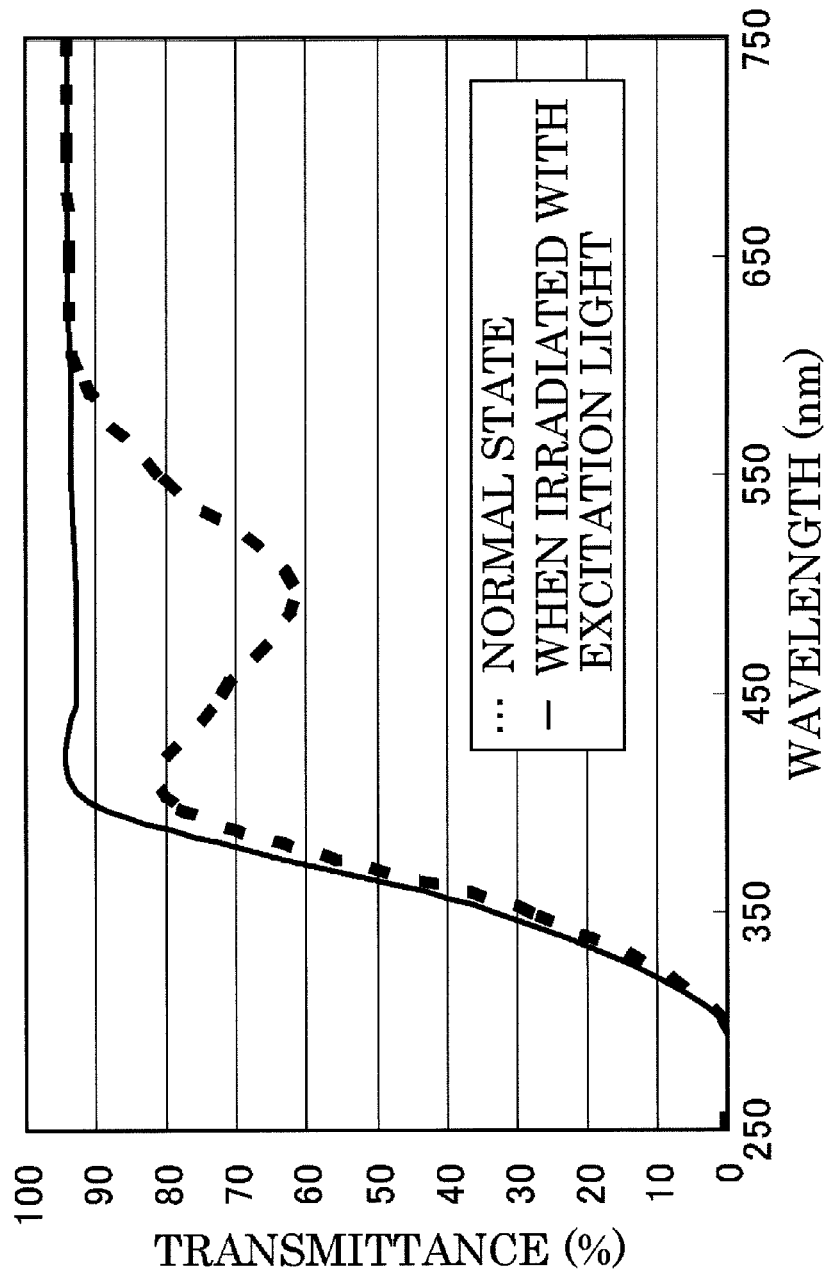
FIG. 4 is a graph showing the ultraviolet-visible light absorption spectra of a compound [1-1] according to Example 1-1 in a normal state and when irradiated with excitation light.

A $1.0 \times 10^{-3}$ M benzene solution was prepared using the mixture containing Compound [1-1] synthesized in Synthesis Example 1-1. This solution was placed in a rectangular quartz cell and irradiated with excitation light from a UV Spot Light Source L8333 (manufactured by Hamamatsu Photonics K. K.) followed by measurement of a colored form and uncolored form by ultraviolet-visible absorption spectroscopy in which the transmittance at the wavelength having the largest change in transmittance in the visible light region was observed. The results are shown in Table 1 and FIG. 4. Furthermore, in FIG. 4, the solid line indicates the state when irradiated with excitation light, while the broken line indicates the normal state (state when not irradiated with excitation light). As shown in Table 1 and FIG. 4, transmittance of the colored form at the wavelength of maximum absorbance of 496 nm increased from 60% to 93% as a result of being irradiated with excitation light.

Example 1-2

Figure 5:
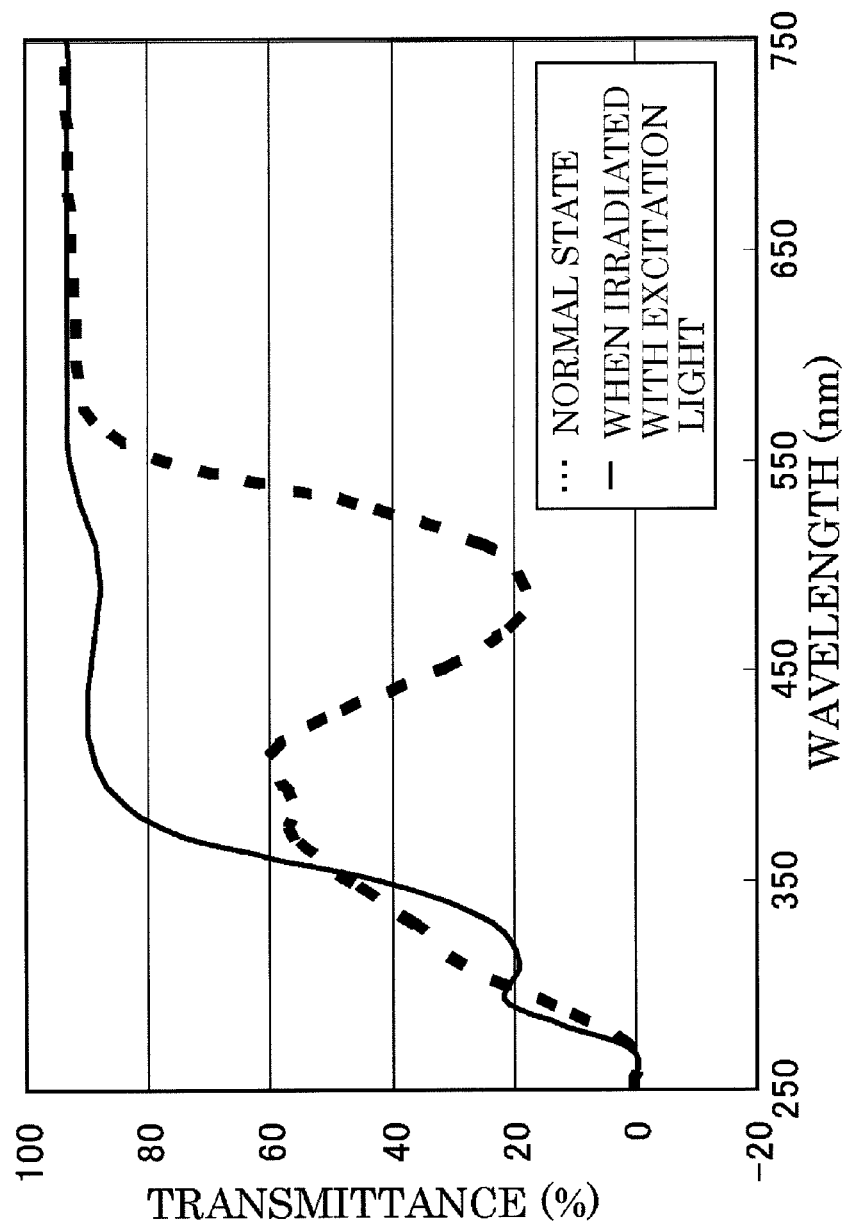
FIG. 5 is a graph showing the ultraviolet-visible light absorption spectra of a compound [1-2] according to Example 1-2 in a normal state and when irradiated with excitation light.

A $2.0 \times 10^{-4}$ M benzene solution was prepared using the Compound [1-2] synthesized in Synthesis Example 1-2. This solution was placed in a rectangular quartz cell and irradiated with excitation light from a UV Spot Light Source L8333 (manufactured by Hamamatsu Photonics K.K.) followed by measurement of a colored form and uncolored form by ultraviolet-visible absorption spectroscopy in which the transmittance at the wavelength having the largest change in transmittance in the visible light region was observed. The results are shown in Table 1 and FIG. 5. Furthermore, in FIG. 5, the solid line indicates the state when irradiated with excitation light, while the broken line indicates the normal state when not irradiated with excitation light. As shown in Table 1 and FIG. 5, transmittance of the colored form at the wavelength of maximum absorbance of 493 nm increased from 17% to 88% as a result of being irradiated with excitation light.

Example 1-3

Figure 6:
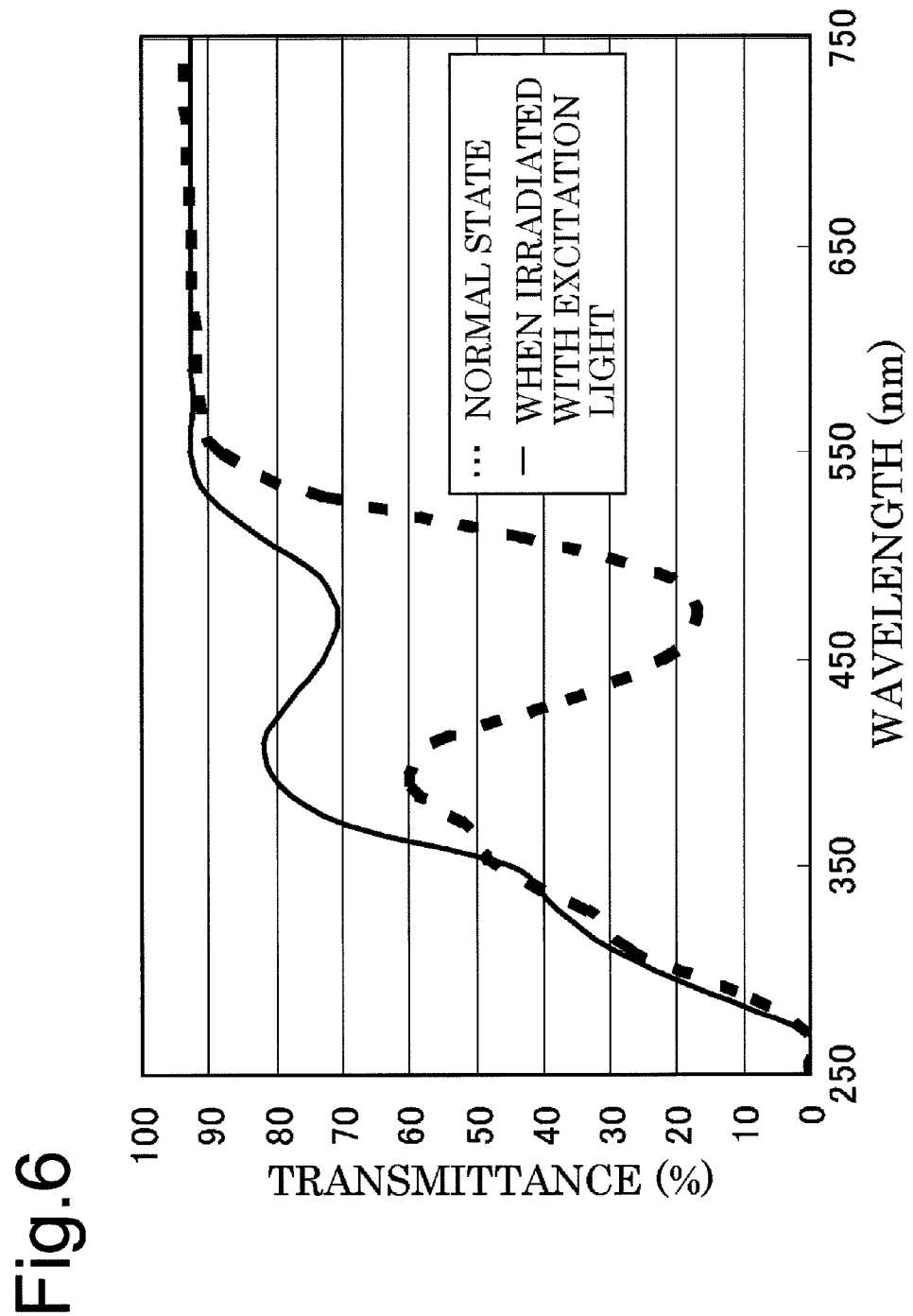
FIG. 6 is a graph showing the ultraviolet-visible light absorption spectra of a compound [1-3] according to Example 1-3 in a normal state and when irradiated with excitation light.

A $2.0 \times 10^{-4}$ M benzene solution was prepared using the Compound [1-3] synthesized in Synthesis Example 1-3. This solution was placed in a rectangular quartz cell and irradiated with excitation light from a UV Spot Light Source L8333 (manufactured by Hamamatsu Photonics K.K.) followed by measurement of a colored form and uncolored form by ultraviolet-visible absorption spectroscopy in which the transmittance at the wavelength having the largest change in transmittance in the visible light region was observed. The results are shown in Table 1 and FIG. 6. Furthermore, in FIG. 6, the solid line indicates the state when irradiated with excitation light, while the broken line indicates the normal state (state when not irradiated with excitation light). As shown in Table 1 and FIG. 6, transmittance of the colored form at the wavelength of maximum absorbance of 475 nm increased from 16% to 73% as a result of being irradiated with excitation light.

Example 1-4

Figure 7:
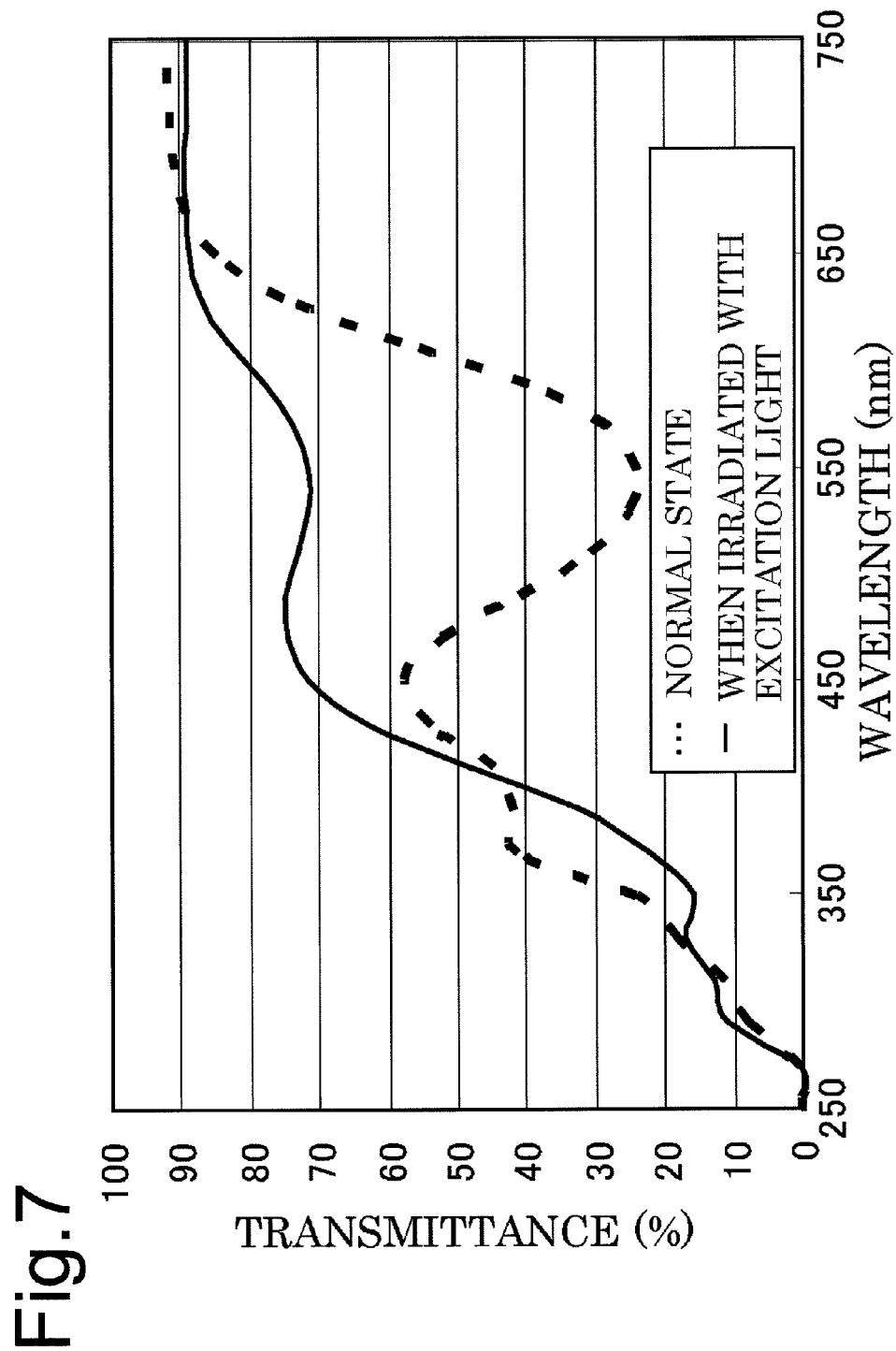
FIG. 7 is a graph showing the ultraviolet-visible light absorption spectra of a compound [1-4] according to Example 1-4 in a normal state and when irradiated with excitation light.

A $2.0 \times 10^{-4}$ M benzene solution was prepared using the Compound [1-4] synthesized in Synthesis Example 1-4. This solution was placed in a rectangular quartz cell and irradiated with excitation light from a UV Spot Light Source L8333 (manufactured by Hamamatsu Photonics K.K.) followed by measurement of a colored form and uncolored form by ultraviolet-visible absorption spectroscopy in which the transmittance at the wavelength having the largest change in transmittance in the visible light region was observed. The results are shown in Table 1 and FIG. 7. Furthermore, in FIG. 7, the solid line indicates the state when irradiated with excitation light, while the broken line indicates the normal state (state when not irradiated with excitation light). As shown in Table 1 and FIG. 7, transmittance of the colored form at the wavelength of maximum absorbance of 544 nm increased from 23% to 74% as a result of being irradiated with excitation light.

Example 1-5

Figure 8:
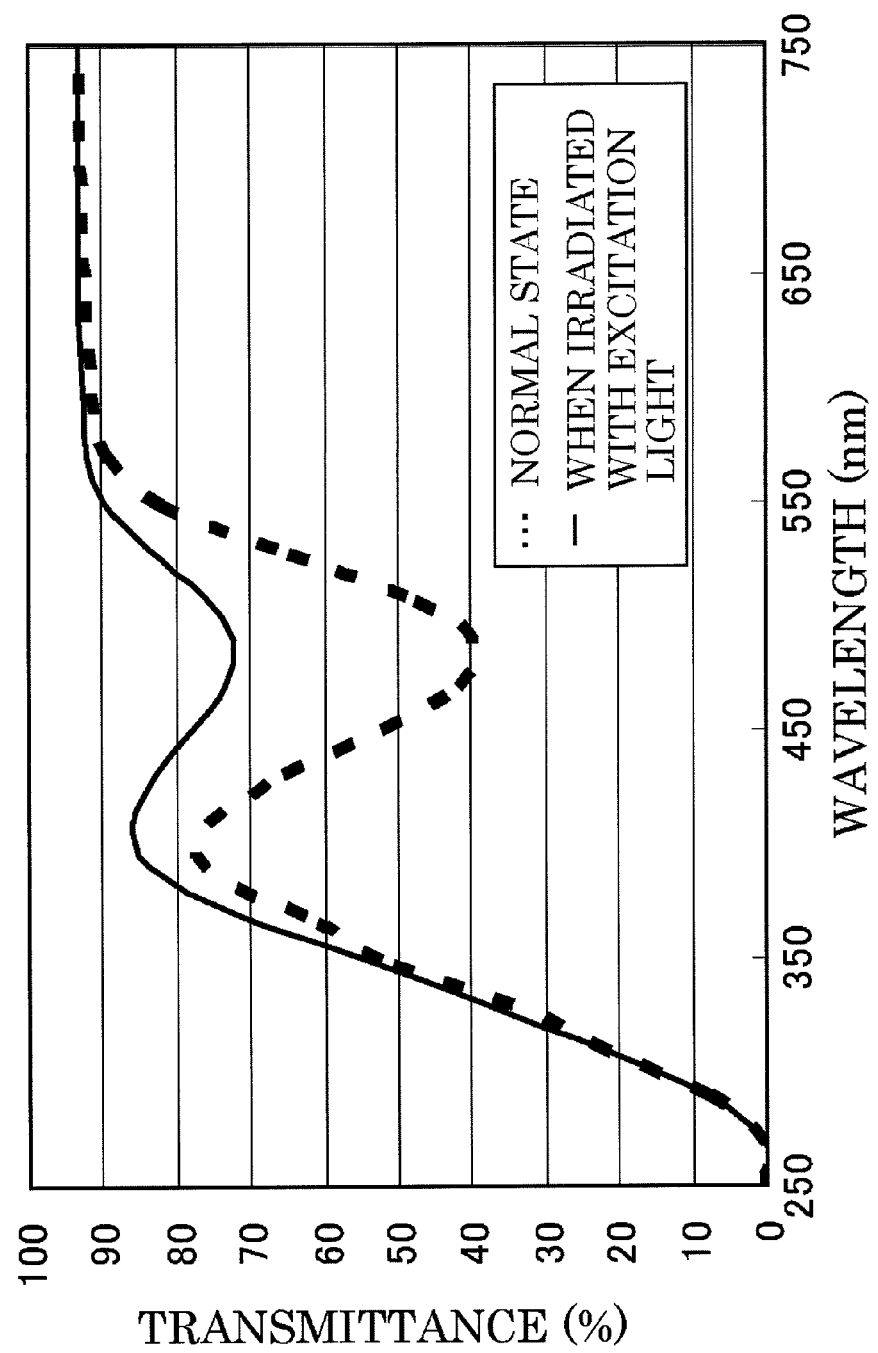
FIG. 8 is a graph showing the ultraviolet-visible light absorption spectra of a compound [1-5] according to Example 1-5 in a normal state and when irradiated with excitation light.

A $2.0 \times 10^{-4}$ M benzene solution was prepared using the Compound [1-5] synthesized in Synthesis Example 1-5. This solution was placed in a rectangular quartz cell and irradiated with excitation light from a UV Spot Light Source L8333 (manufactured by Hamamatsu Photonics K.K.) followed by measurement of a colored form and uncolored form by ultraviolet-visible absorption spectroscopy in which the transmittance at the wavelength having the largest change in transmittance in the visible light region was observed. The results are shown in Table 1 and FIG. 8. Furthermore, in FIG. 8, the solid line indicates the state when irradiated with excitation light, while the broken line indicates the normal state (state when not irradiated with excitation light). As shown in Table 1 and FIG. 8, transmittance of the colored form at the wavelength of maximum absorbance of 486 nm increased from 39% to 74% as a result of being irradiated with excitation light.

Comparative Example 1-1

Figure 9:
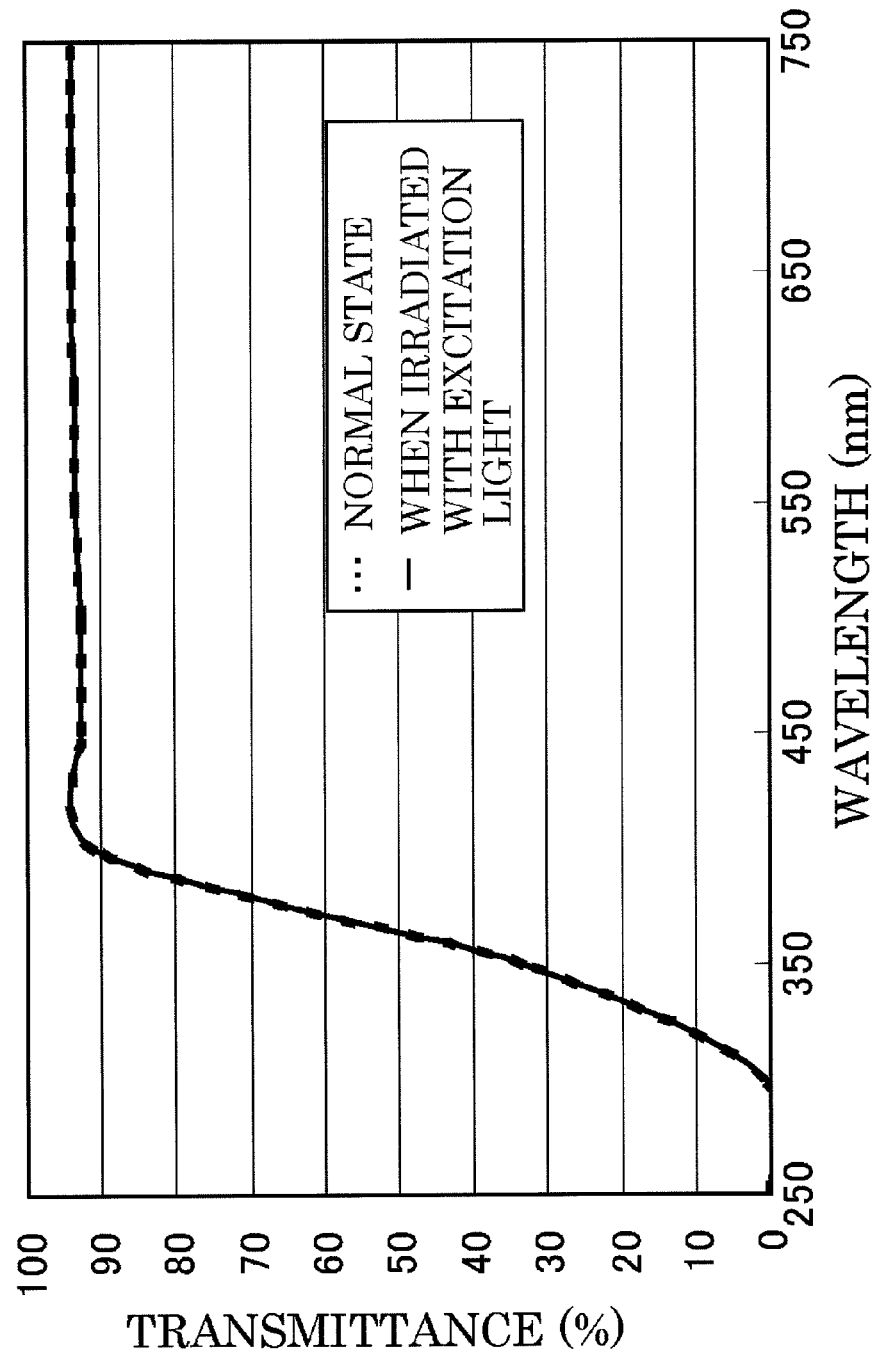
FIG. 9 is a graph showing the ultraviolet-visible light absorption spectra of a compound [1-6] according to Comparative Example 1-1 in a normal state and when irradiated with excitation light.

A $2.0 \times 10^{-4}$ M benzene solution was prepared using the Compound [1-6] synthesized in Synthesis Example 1-6. This solution was placed in a rectangular quartz cell and irradiated with excitation light from a UV Spot Light Source L8333 (manufactured by Hamamatsu Photonics K. K.) followed by measurement of transmittance in a state when not irradiated with excitation light and transmittance in a state when irradiated with excitation light by ultraviolet-visible absorption spectroscopy. The results are shown in Table 1 and FIG. 9. Furthermore, in FIG. 9, the solid line indicates the state when irradiated with excitation light, while the broken line indicates the normal state (state when not irradiated with excitation light). As shown in Table 1 and FIG. 9, transmittance did not change from 93% even when irradiated with excitation light.

TABLE 1

| | Wavelength of maximum absorbance of colored form (nm) | Transmittance of colored form (%) | Transmittance of uncolored form (%) |
|---|---|---|---|
| Example 1-1 | 496 | 60 | 93 |
| Example 1-2 | 493 | 17 | 88 |
| Example 1-3 | 475 | 16 | 73 |
| Example 1-4 | 544 | 23 | 74 |
| Example 1-5 | 486 | 39 | 74 |
| Comparative Example 1-1 | 500 | 93 | 93 |

According to the results shown in Table 1, molecules demonstrating reverse photochromic properties were determined to be obtained by introducing sterically bulky substituents into $R_4$ and $R_5$ of a biimidazole compound represented by general formula (1-1).

The following provides a specific explanation of examples corresponding to the second embodiment of the present invention.

Synthesis Example 2-1

100 mg of 6,6'-dimethyl-2,2'-diformylbiphenyl, 270 mg of 4,4'-dimethoxybenzyl, 960 mg of ammonium acetate and 4.0 ml of acetic acid were mixed, and after allowing to react by heating and stirring for 16 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 273 mg of an intermediate (1-I). Formation of the intermediate (1-I) was confirmed by NMR analysis.

[Chemical Formula 25]

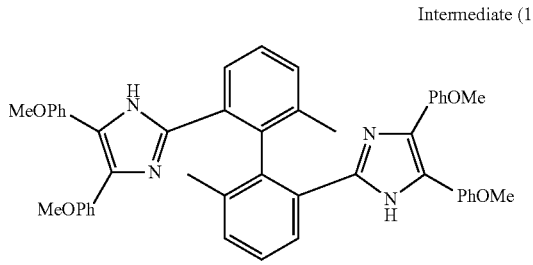

Intermediate (1-I)

120 mg of the above-mentioned intermediate (1-I) were dissolved in 25 ml of benzene followed by the addition of a solution obtained by dissolving 4.1 g of potassium ferricyanide and 1.8 g of potassium hydroxide in 30 ml of water in the presence of nitrogen and under protection from light, and after allowing to react by stirring for 2 hours at room temperature, the aqueous layer was separated and extracted with benzene, and recrystallization was carried out by concentrating the solvent to obtain 89 mg of Compound [2-1] alone. It was confirmed by NMR analysis that Compound [2-1] was represented by the following structural formula. Furthermore, the results of NMR analysis were as shown below.

1H-NMR (500 MHz, CDCl$_3$): 7.43 (2H,s), 7.41 (4H, d), 7.36 (4H, d), 7.13 (2H, t), 6.83 (2H, d), 6.80 (4H, d), 6.75 (4H, d), 3.81 (6H,s), 3.77 (6H,s), 2.48 (6H,s)

13C-NMR (500 MHz, CDCl$_3$): 169.9, 164.9, 161.14, 161.09, 136.1, 135.4, 134.9, 131.2, 130.6, 128.3, 126.7, 125.4, 125.0, 121.6, 113.5, 113.3, 106.7, 55.3, 55.2, 21.3

[Chemical Formula 26]

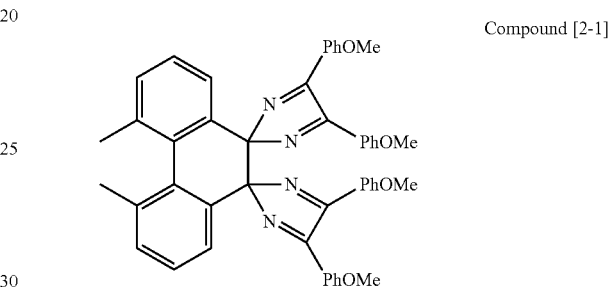

Compound [2-1]

Next, 30 mg of Compound [2-1] obtained in the manner described above were dissolved in 5 ml of deuterated chloroform and allowed to stand for 3 days at 25° C. under protection from light to obtain 30 mg of the following Compound [2-3] alone. Formation of Compound [2-3] was confirmed by NMR analysis. Furthermore, the results of NMR analysis were as indicated below.

1H-NMR (500 MHz, CDCl$_3$): 7.96 (1H, d), 7.64 (1H, d), 7.58 (1H, d), 7.39 (1H, t), 7.35 (1H, d), 7.28 (2H, d), 7.26 (1H, d), 7.19 (1H, t), 7.16 (2H, d), 7.11 (1H, d), 6.90 (2H, d), 6.85 (1H, d), 6.73 (2H, d), 6.71 (2H, d), 6.70 (1H, d), 6.67 (2H, d), 3.90 (3H,s), 3.83 (3H,s), 3.76 (3H,s), 3.71 (3H,s), 2.28 (3H,s), 2.23 (3H,s)

[Chemical Formula 27]

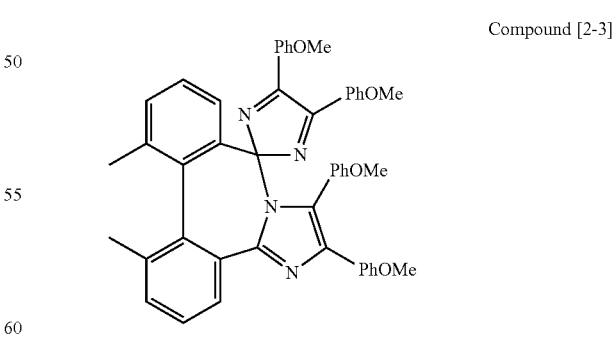

Compound [2-3]

Furthermore, a mixture of Compound [2-1] and the following Compound [1-1] and Compound [2-3] was obtained by dissolving 30 mg of Compound [2-1] in 5 ml of deuterated chloroform and allowing to stand for 1 day at 25° C. under protection from light. These compounds were present in the mixture at a ratio of Compound [2-1] to Compound [1-1] to Compound [2-3] of 10:15:75. Compound [1-1] was determined to exhibit the characteristic peaks of a methoxy group and methyl group based on NMR analysis of the mixture, and since Compound [1-1] exhibited a characteristic absorption band at 496 nm based on UV spectral analysis, it was thought to clearly have the structure represented by the structural formula indicated below.

[Chemical Formula 28]

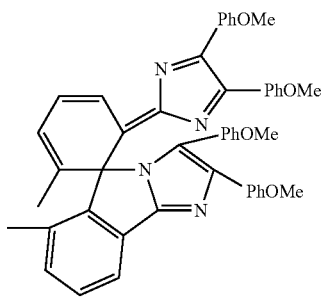

Compound [1-1]

Example 2-1

Figure 10:
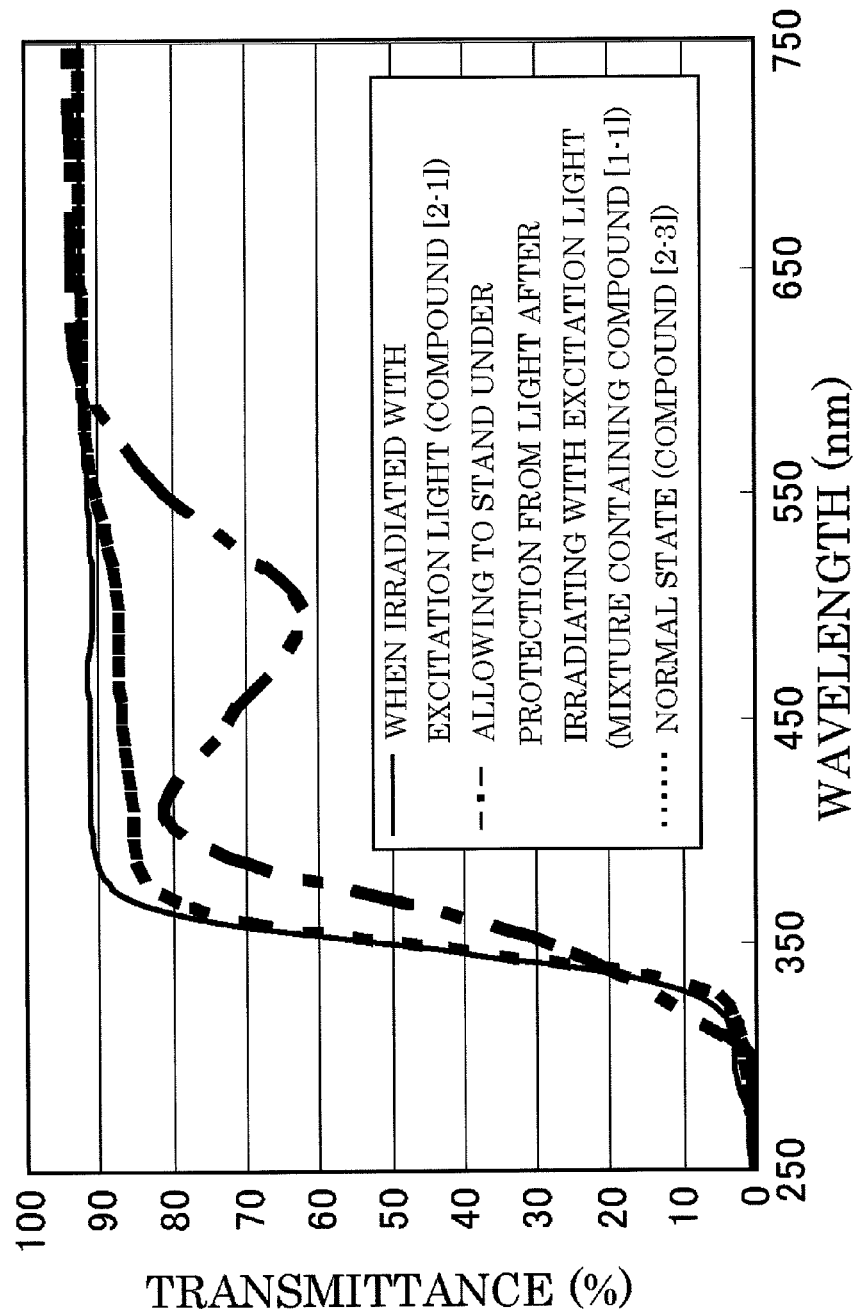
FIG. 10 is a graph showing the ultraviolet-visible light absorption spectra of a compound [2-3] according to Example 2-1 in a normal state, when irradiated with excitation light, and when protected from light after having irradiated with excitation light.

A 1.0×10⁻³ M benzene solution was prepared using Compound [2-3] synthesized in Synthesis Example 2-1. The transmittance of this benzene solution was measured by ultraviolet-visible absorption spectroscopy. The results are shown in FIG. 10. In addition, the above-mentioned benzene solution was placed in a rectangular quartz cell and irradiated with excitation light in the form of ultraviolet-visible light from a UV Spot Light Source L8333 (manufactured by Hamamatsu Photonics K. K.) followed by measurement of transmittance of the benzene solution while in this state by ultraviolet-visible absorption spectroscopy. The results are shown in FIG. 10. In addition, after irradiating the above-mentioned benzene solution with excitation light in the form of ultraviolet-visible light from a UV Spot Light Source L8333 (manufactured by Hamamatsu Photonics K.K.), the benzene solution was allowed to stand for 1 day at 25° C. under protection from light, and transmittance of the benzene solution was measured while in that state by ultraviolet-visible absorption spectroscopy. The results are shown in FIG. 10. Furthermore, in FIG. 10, the broken line indicates the normal state (state when not irradiated with excitation light), the solid line indicates the state when irradiated with excitation light, and the single-dot broken line indicates the state when allowed to stand for 1 day at 25° C. under protection from light after being irradiated with excitation light. As shown in FIG. 10, transmittance of Compound [2-3] at the wavelength of maximum absorption of the mixture containing the colored form in the form of Compound [1-1] of 496 nm decreased from 87% to 60% as a result of allowing to stand under protection from light after being irradiated with excitation light. On the basis thereof, Compound [2-3] was determined to have changed to the mixture containing Compound [1-1] as a result of being allowed to stand under protection from light after being irradiated with excitation light. Similarly, transmittance of Compound [2-3] at 496 nm increased from 87% to 91% as a result of being irradiated with excitation light. On the basis thereof, Compound [2-3] was determined to have changed to Compound [2-1] as a result of being irradiated with excitation light.

According to the results indicated in Example 2-1 and Comparative Example 1-1, a molecule demonstrating photochromic properties was confirmed to be obtained by introducing sterically bulky substituents into $R_4$ and $R_5$ of a biimidazole compound represented by general formula (1).

The following provides a specific explanation of examples corresponding to the third embodiment of the present invention.

Synthesis Example 3-1

100 mg of 6,6'-dimethyl-2,2'-diformylbiphenyl, 270 mg of 4,4'-dimethoxybenzyl, 960 mg of ammonium acetate and 4.0 ml of acetic acid were mixed, and after allowing to react by heating and stirring for 16 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 273 mg of an intermediate (1-I). Formation of the intermediate (1-I) was confirmed by NMR analysis.

[Chemical Formula 29]

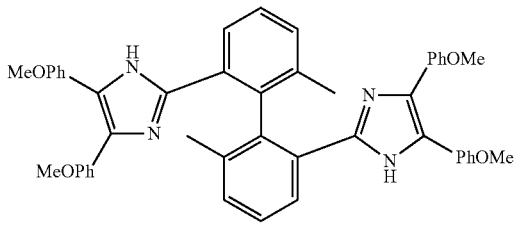

Intermediate (1-I)

120 mg of the above-mentioned intermediate (1-I) were dissolved in 25 ml of benzene followed by the addition of a solution obtained by dissolving 4.1 g of potassium ferricyanide and 1.8 g of potassium hydroxide in 30 ml of water in the presence of nitrogen and under protection from light, and after allowing to react by stirring for 2 hours at room temperature, the aqueous layer was separated and extracted with benzene, and recrystallization was carried out by concentrating the solvent to obtain 102 mg of a mixture containing 24 mg of Compound [1-1]. The formation of Compound [1-1] was confirmed by NMR analysis. Furthermore, although NMR analysis was carried out on the mixture and results for NMR analysis of Compound [1-1] alone were not obtained, since the results indicated the characteristic peaks of a methoxy group and methyl group and the mixture demonstrated a characteristic absorption band at 496 nm in the UV spectrum thereof, Compound [1-1] in the mixture was thought to be clearly represented by the structural formula indicated below.

[Chemical Formula 30]

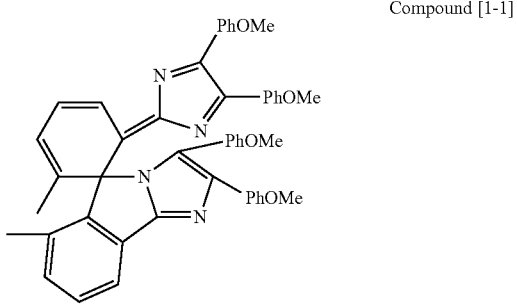

Compound [1-1]

Continuing, Compound [1-1] was dissolved in deuterated chloroform and irradiated with visible light for 300 seconds at 25° C. Subsequently, the formation of Compound [2-1] was confirmed by NMR analysis.

[Chemical Formula 31]

Compound [2-1]

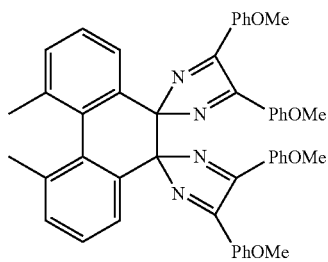

Synthesis Example 3-2

100 mg of 2,2'-diformyl-1,1'-binaphthalene, 183 mg of 4,4'-dimethoxybenzyl, 750 mg of ammonium acetate and 4.0 ml of acetic acid were mixed, and after allowing to react by heating and stirring for 14 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 158 mg of an intermediate (1-II). Formation of the intermediate (1-II) was confirmed by NMR analysis.

[Chemical Formula 32]

Intermediate (1-II)

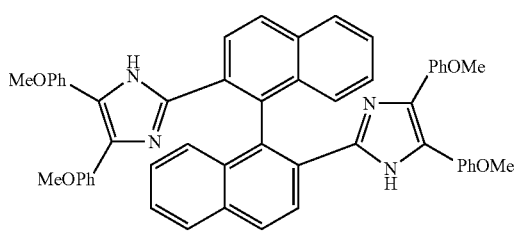

84 mg of the above-mentioned intermediate (1-II) were dissolved in 25 ml of benzene followed by the addition of a solution obtained by dissolving 2.5 g of potassium ferricyanide and 1.1 g of potassium hydroxide in 20 ml of water in the presence of nitrogen and under protection from light, and after allowing to react by stirring for 2 hours at room temperature, the aqueous layer was separated and extracted with benzene, and recrystallization was carried out by concentrating the solvent to obtain 79 mg of Compound [1-2]. The formation of Compound [1-2] was confirmed by NMR analysis and X-ray crystal structure analysis.

[Chemical Formula 33]

Compound [1-2]

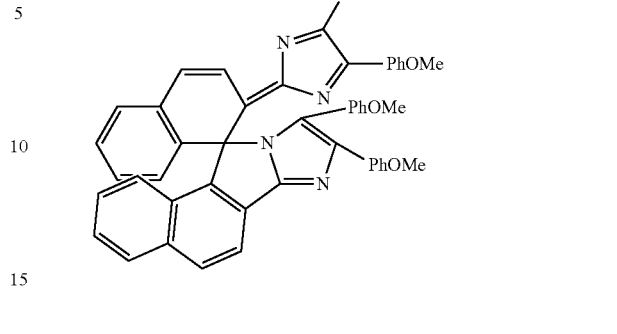

Continuing, Compound [1-2] was dissolved in deuterated chloroform and irradiated with visible light for 300 seconds at −78° C. Subsequently, the formation of Compound [3-1] was confirmed by NMR analysis under conditions of cooling to −50° C. Furthermore, the results of NMR analysis were as indicated below.

1H-NMR (500 MHz, CDCl$_3$): 7.97 (2H, d), 7.87 (2H, d), 7.82 (2H, d), 7.56 (2H, t), 7.46-7.42 (8H, m), 7.41 (2H, t), 7.23 (2H, d), 6.89 (4H, d), 6.75 (4H, d), 3.88 (6H,s), 3.79 (6H,s)

13C-NMR (500 MHz, CDCl$_3$): 170.5, 165.4, 160.7, 160.6, 137.9, 134.0, 133.3, 132.5, 131.4, 131.3, 130.6, 130.5, 128.0, 125.3, 124.6, 124.5, 123.8, 122.4, 113.2, 112.7, 106.3, 55.3, 55.2

[Chemical Formula 34]

Compound [3-1]

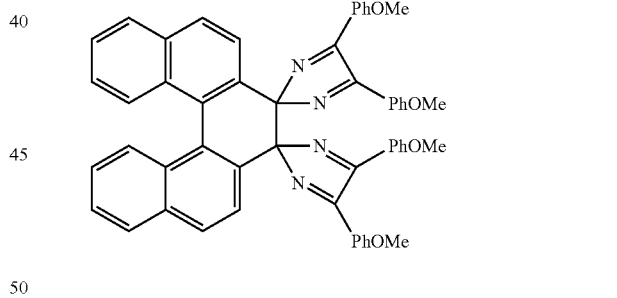

Synthesis Example 3-3

100 mg of 2,2'-diformyl-1,1'-binaphthalene, 149 mg of benzyl, 750 mg of ammonium acetate and 4.0 ml of acetic acid were mixed, and after allowing to react by heating and stirring for 14 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 162 mg of an intermediate (1-III). Formation of the intermediate (1-III) was confirmed by NMR analysis.

[Chemical Formula 35]

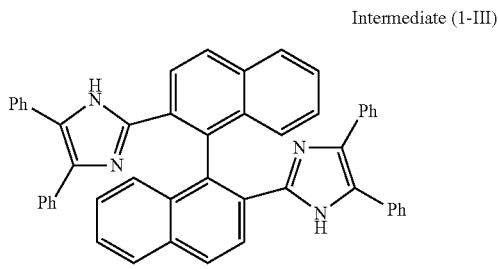

Intermediate (1-III)

87 mg of the above-mentioned intermediate (1-III) were dissolved in 25 ml of benzene followed by the addition of a solution obtained by dissolving 2.9 g of potassium ferricyanide and 1.3 g of potassium hydroxide in 20 ml of water in the presence of nitrogen and under protection from light, and after allowing to react by stirring for 2 hours at room temperature, the aqueous layer was separated and extracted with benzene, and recrystallization was carried out by concentrating the solvent to obtain 75 mg of Compound [1-3]. The formation of Compound [1-3] was confirmed by NMR analysis.

[Chemical Formula 36]

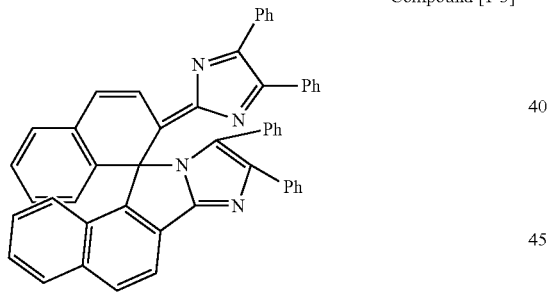

Compound [1-3]

Synthesis Example 3-4

100 mg of 2,2'-diformyl-1,1'-binaphthalene, 210 mg of 4,4'-bis(dimethylamino)benzyl, 750 mg of ammonium acetate and 4.0 ml of acetic acid were mixed, and after allowing to react by heating and stirring for 18 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 114 mg of an intermediate (1-IV). Formation of the intermediate (1-IV) was confirmed by NMR analysis.

[Chemical Formula 37]

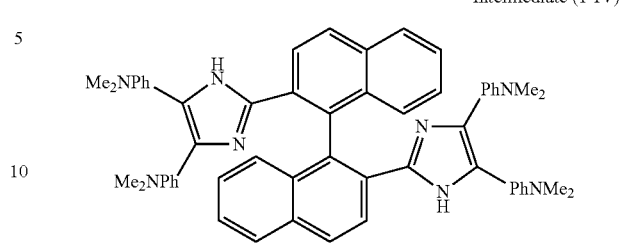

Intermediate (1-IV)

80 mg of the above-mentioned intermediate (1-IV) were dissolved in 25 ml of benzene followed by the addition of a solution obtained by dissolving 2.3 g of potassium ferricyanide and 1.0 g of potassium hydroxide in 20 ml of water in the presence of nitrogen and under protection from light, and after allowing to react by stirring for 2 hours at room temperature, the aqueous layer was separated and extracted with benzene and a solid was precipitated by concentrating the solvent. Recrystallization was carried out by dissolving the precipitated solid in ethanol to obtain 59 mg of Compound [1-4]. The formation of Compound [1-4] was confirmed by NMR analysis.

[Chemical Formula 38]

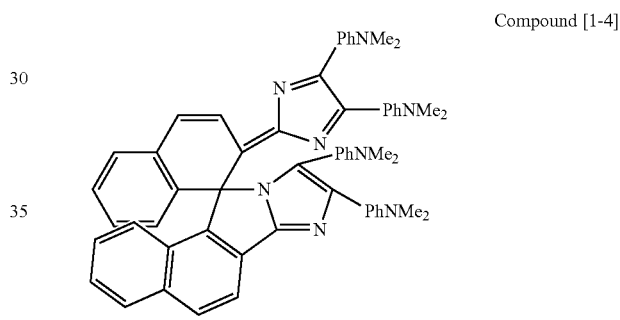

Compound [1-4]

Synthesis Example 3-5

100 mg of 2,2'-diformyl-1,1'-binaphthalene, 261 mg of 4,4'-dibromobenzyl, 750 mg of ammonium acetate and 4.0 ml of acetic acid were mixed, and after allowing to react by heating and stirring for 18 hours in an oil bath at 110° C., 8.0 ml of 28% aqueous ammonia were added to neutralize while precipitating a solid followed by rinsing the solid with water, filtering and drying with a vacuum dryer. The dried solid was then purified by separating with a silica gel column followed by concentrating the solvent to obtain 249 mg of an intermediate (1-V). Formation of the intermediate (1-V) was confirmed by NMR analysis.

[Chemical Formula 39]

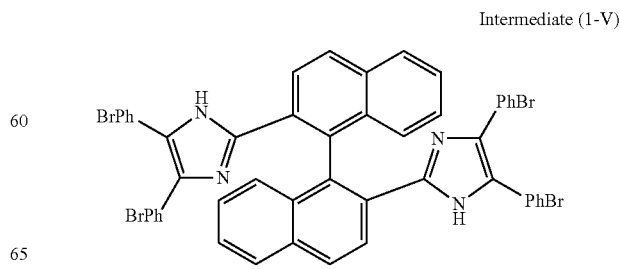

Intermediate (1-V)

80 mg of the above-mentioned intermediate (1-V) were dissolved in 10 ml of benzene followed by the addition of a solution obtained by dissolving 2.0 g of potassium ferricyanide and 0.90 g of potassium hydroxide in 15 ml of water in the presence of nitrogen and under protection from light, and after allowing to react by stirring for 2 hours at room temperature, the aqueous layer was separated and extracted with benzene and a solid was precipitated by concentrating the solvent. Recrystallization was carried out by dissolving the precipitated solid in ethanol to obtain 22 mg of Compound [1-5] composed of a reverse photochromic molecule. The formation of Compound [1-5] was confirmed by NMR analysis.

[Chemical Formula 40]

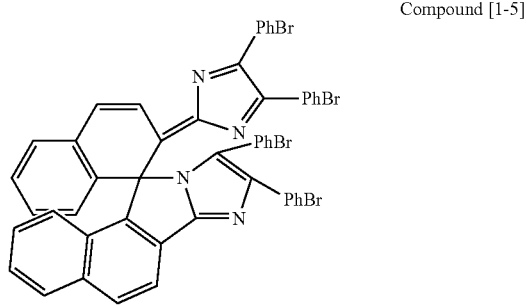

Compound [1-5]

Example 3-1

A 1.0×10$^{-3}$ M benzene solution was prepared using the mixture containing Compound [1-1] synthesized in Synthesis Example 3-1. This solution was placed in a rectangular quartz cell and irradiated with visible light for 30 seconds at 25° C.

The absorption spectrum of Compound [2-1] (uncolored form) was measured by ultraviolet-visible absorption spectroscopy while continuing to irradiate with visible light. The results are shown in Table 2 and FIG. 11. Furthermore, in FIG. 11, the solid line indicates the absorption spectrum of Compound [2-1].

Continuing, a benzene solution containing the above-mentioned Compound [2-1] was allowed to stand for 1 day at 25° C. under protection from light by discontinuing irradiation with visible light. The absorption spectrum of the benzene solution while in this state was then measured by ultraviolet-visible absorption spectroscopy. The results are shown in Table 2 and FIG. 11. Furthermore, these results are indicated with the broken line in FIG. 11. On the basis of NMR analysis, the above-mentioned benzene solution demonstrated the characteristic peaks of a methoxy group and methyl group and demonstrated the characteristic absorption band at 496 nm based on analysis of the UV spectrum thereof. On the basis thereof, the above-mentioned benzene solution was thought to clearly contain Compound [1-1].

Figure 11:
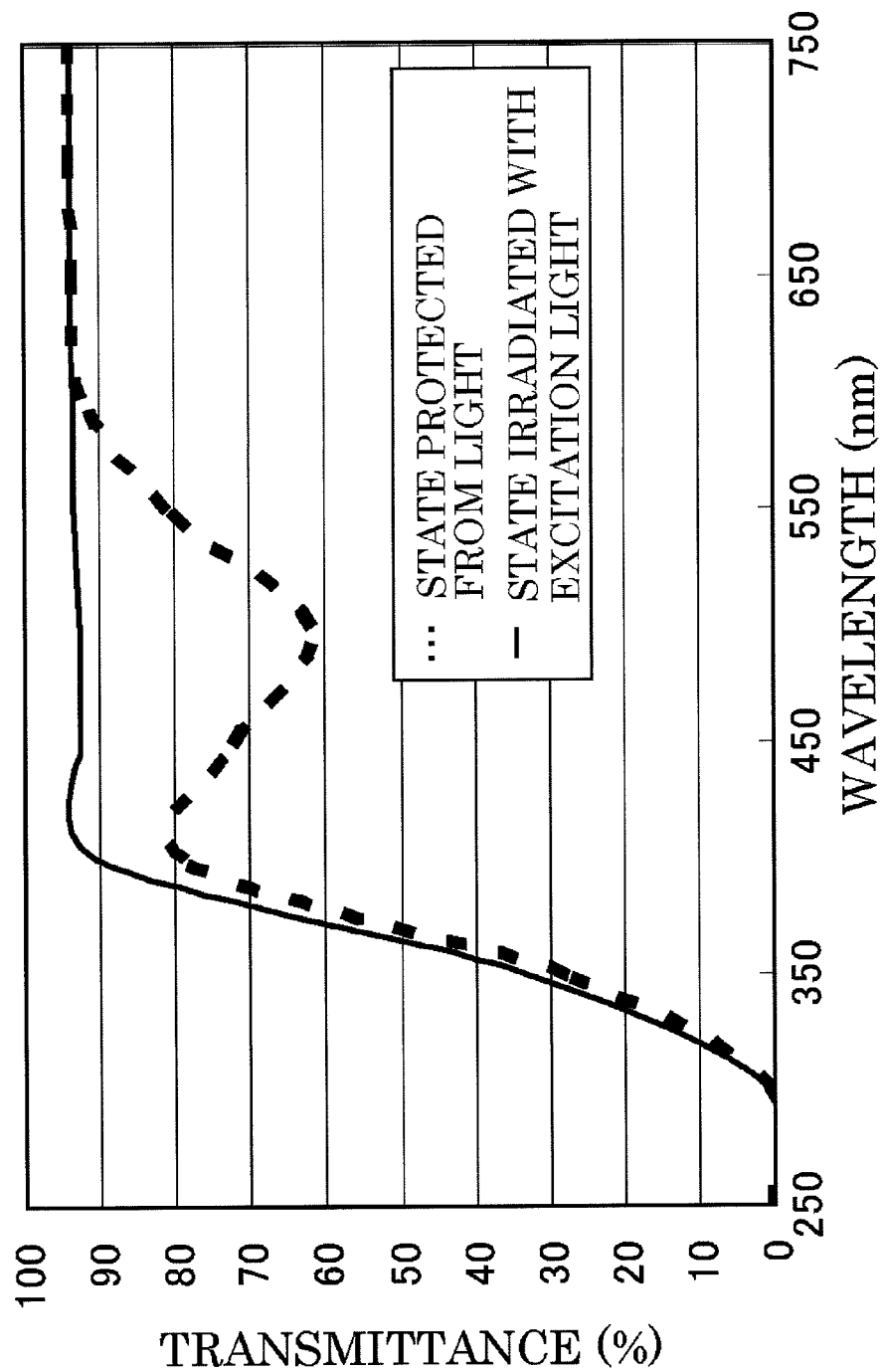
FIG. 11 is a graph showing the ultraviolet-visible light absorption spectra of a compound [2-1] according to Example 3-1 when irradiated with light and when protected from light.

As is shown in Table 2 and FIG. 11, transmittance of the uncolored form at the wavelength of maximum absorbance of the colored form of 496 nm was determined to have decreased from 93% to 60% as a result of allowing to stand under protection from light.

Example 3-2

A 2.0×10$^{-4}$ M benzene solution was prepared using Compound [1-2] synthesized in Synthesis Example 3-2. This solution was placed in a rectangular quartz cell and irradiated with visible light for 30 seconds at 25° C.

The absorption spectrum of Compound [3-1] (uncolored form) was measured by ultraviolet-visible absorption spectroscopy while continuing to irradiate with visible light. The results are shown in Table 2 and FIG. 12. Furthermore, in FIG. 12, the solid line indicates the absorption spectrum of Compound [3-1].

Continuing, a benzene solution containing the above-mentioned Compound [3-1] was allowed to stand for 10 minutes at 25° C. under protection from light by discontinuing irradiation with visible light. The absorption spectrum of the benzene solution while in this state was then measured by ultraviolet-visible absorption spectroscopy. The results are shown in Table 2 and FIG. 12. Furthermore, these results are indicated with the broken line in FIG. 12.

Figure 12:
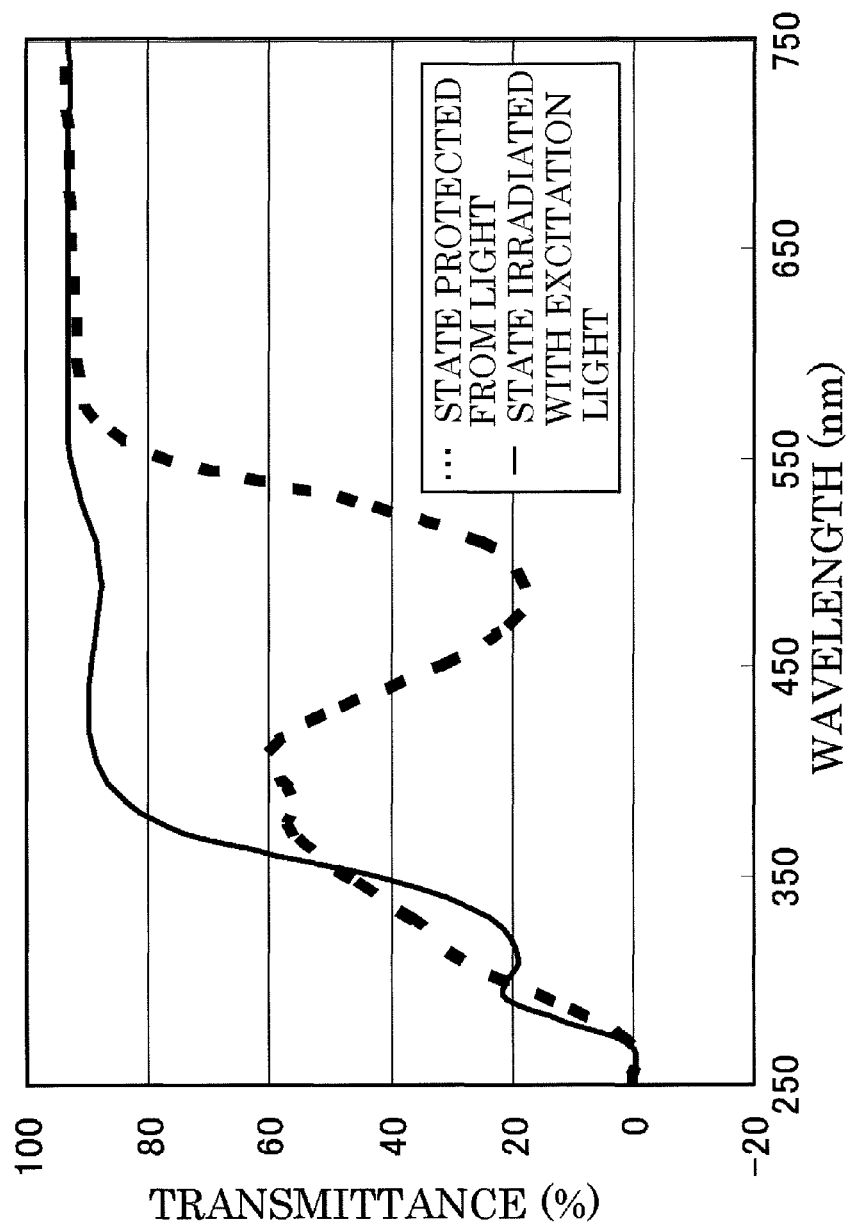
FIG. 12 is a graph showing the ultraviolet-visible light absorption spectra of a compound [3-1] according to Example 3-2 when irradiated with light and when protected from light.

As is shown in Table 2 and FIG. 12, transmittance of Compound [3-1] (uncolored form) at the wavelength of maximum absorbance of the colored form of 493 nm was determined to have decreased from 88% to 17%. In addition, the absorption spectrum indicated with the broken line in FIG. 12 was similar to the absorption spectrum of Compound [1-2]. On the basis thereof, Compound [3-1] was determined to have changed to Compound [1-2] as a result of allowing to stand under protection from light.

Example 3-3

A 2.0×10$^{-4}$ M benzene solution was prepared using Compound [1-3] synthesized in Synthesis Example 3-3. This solution was placed in a rectangular quartz cell and irradiated with visible light for 30 seconds at 25° C. At this time, formation of the following Compound [3-2] was confirmed since a change in the UV spectrum similar to that in Example 3-2 was observed.

[Chemical Formula 41]

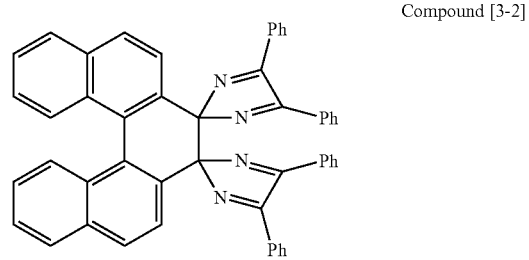

Compound [3-2]

The absorption spectrum of Compound [3-2] (uncolored form) was measured by ultraviolet-visible absorption spectroscopy while continuing to irradiate with visible light. The results are shown in Table 2 and FIG. 13. Furthermore, in FIG. 13, the solid line indicates the absorption spectrum of Compound [3-2].

Continuing, a benzene solution containing the above-mentioned Compound [3-2] was allowed to stand for 10 minutes at 25° C. under protection from light by discontinuing irradiation with visible light. The absorption spectrum of the benzene solution while in this state was then measured by ultraviolet-visible absorption spectroscopy. The results are shown in Table 2 and FIG. 13. Furthermore, these results are indicated with the broken line in FIG. 13.

Figure 13:
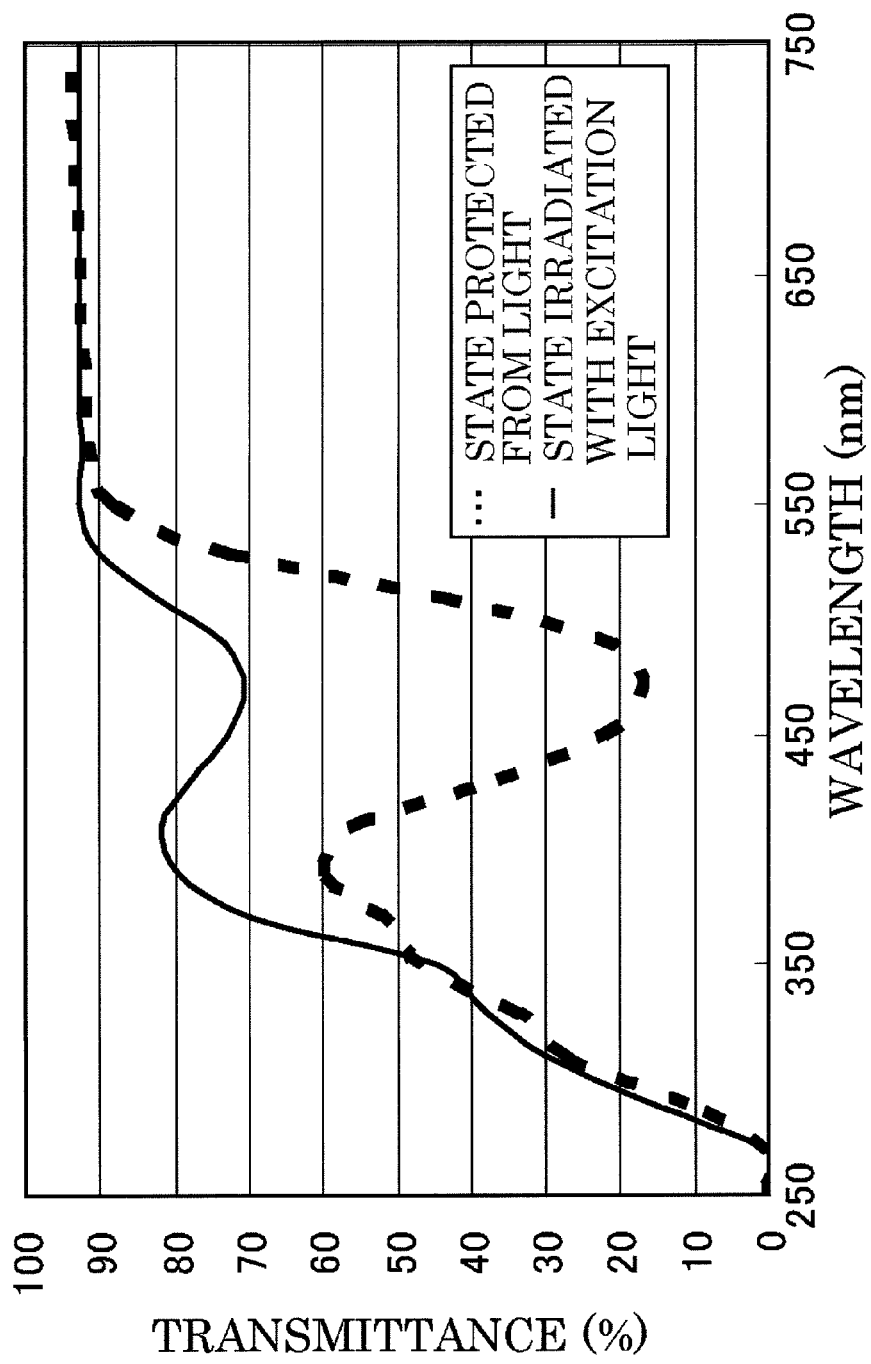
FIG. 13 is a graph showing the ultraviolet-visible light absorption spectra of a compound [3-2] according to Example 3-3 when irradiated with light and when protected from light.

As is shown in Table 2 and FIG. 13, transmittance of Compound [3-2] (uncolored form) at the wavelength of maximum absorbance of the colored form of 475 nm was determined to have decreased from 73% to 16% as a result of allowing to stand under protection from light. In addition, the absorption spectrum indicated with the broken line in FIG. 13 was similar to the absorption spectrum of Compound [1-3]. On the basis thereof, Compound [3-2] was determined to have changed to Compound [1-3] as a result of allowing to stand under protection from light.

Example 3-4

A $2.0 \times 10^{-4}$ M benzene solution was prepared using Compound [1-4] synthesized in Synthesis Example 3-4. This solution was placed in a rectangular quartz cell and irradiated with visible light for 30 seconds at 25° C. At this time, formation of the following Compound [3-3] was confirmed since a change was observed in the UV spectrum similar to that in Synthesis Example 3-2 was observed.

[Chemical Formula 42]

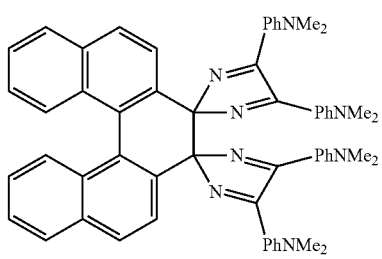

Compound [3-3]

The absorption spectrum of Compound [3-3] (uncolored form) was measured by ultraviolet-visible absorption spectroscopy while continuing to irradiate with visible light. The results are shown in Table 2 and FIG. 14. Furthermore, in FIG. 14, the solid line indicates the absorption spectrum of Compound [3-3].

Continuing, a benzene solution containing the above-mentioned Compound [3-3] was allowed to stand for 10 minutes at 25° C. under protection from light by discontinuing irradiation with visible light. The absorption spectrum of the benzene solution while in this state was then measured by ultraviolet-visible absorption spectroscopy. The results are shown in Table 2 and FIG. 14. Furthermore, these results are indicated with the broken line in FIG. 14.

Figure 14:
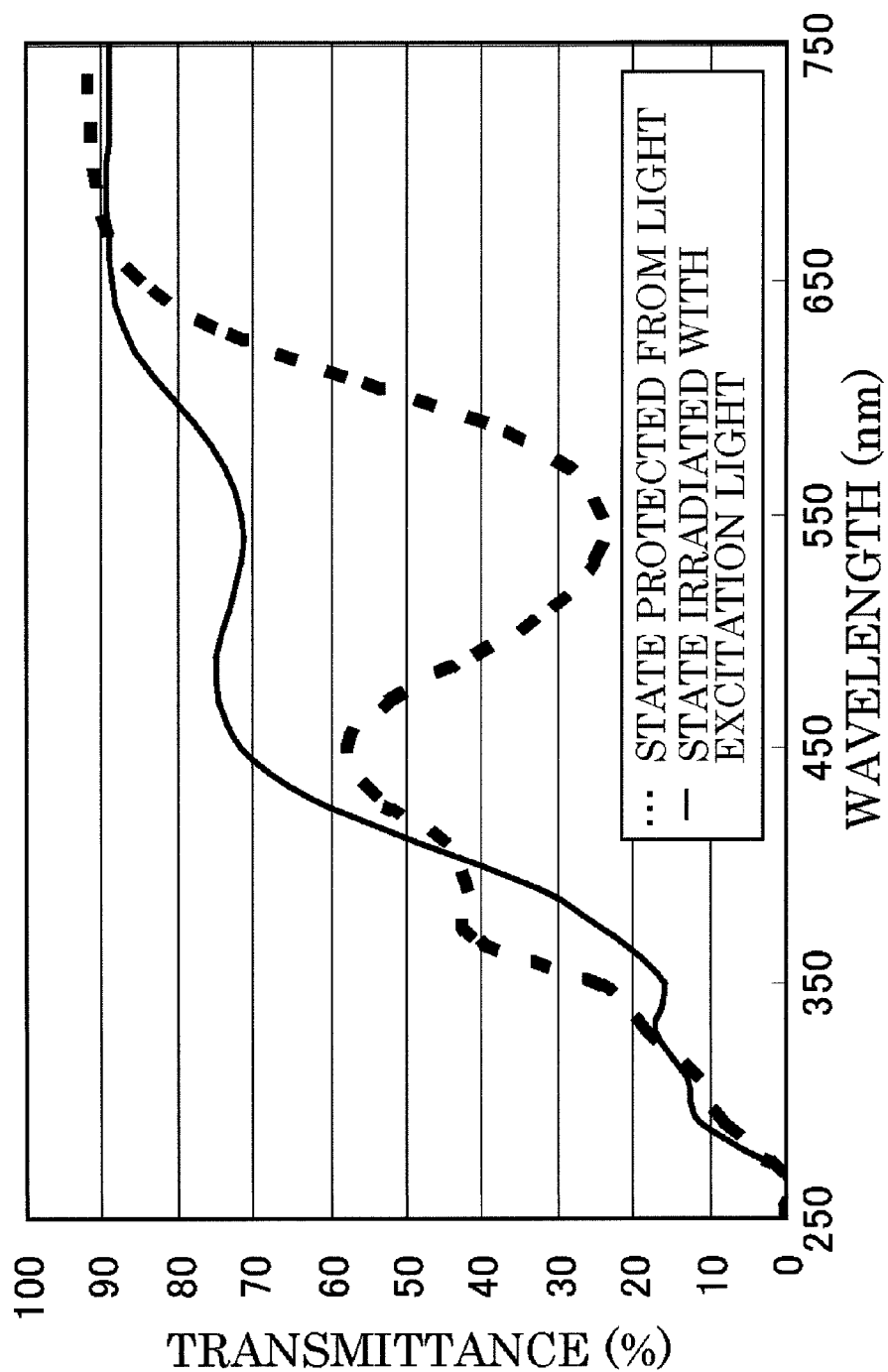
FIG. 14 is a graph showing the ultraviolet-visible light absorption spectra of a compound [3-3] according to Example 3-4 when irradiated with light and when protected from light.

As is shown in Table 2 and FIG. 14, transmittance of Compound [3-3] (uncolored form) at the wavelength of maximum absorbance of the colored form of 544 nm was determined to have decreased from 74% to 23% as a result of allowing to stand under protection from light. In addition, the absorption spectrum indicated with the broken line in FIG. 14 was similar to the absorption spectrum of Compound [1-4]. On the basis thereof, Compound [3-3] was determined to have changed to Compound [1-4] as a result of allowing to stand under protection from light.

Example 3-5

A $2.0 \times 10^{-4}$ M benzene solution was prepared using Compound [1-5] synthesized in Synthesis Example 3-5. This solution was placed in a rectangular quartz cell and irradiated with visible light for 30 seconds at 25° C. At this time, formation of the following Compound [3-4] was confirmed since a change was observed in the UV spectrum similar to that in Synthesis Example 3-2 was observed.

[Chemical Formula 43]

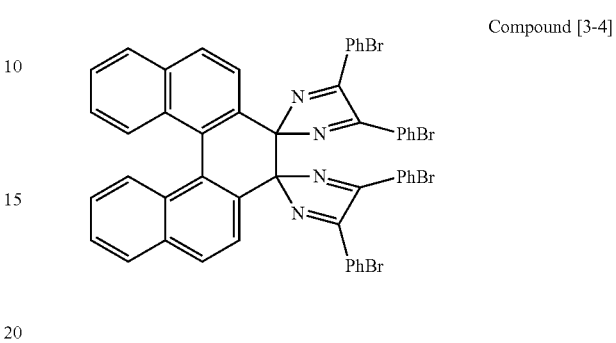

Compound [3-4]

The absorption spectrum of Compound [3-4] (uncolored form) was measured by ultraviolet-visible absorption spectroscopy while continuing to irradiate with visible light. The results are shown in Table 2 and FIG. 15. Furthermore, in FIG. 15, the solid line indicates the absorption spectrum of Compound [3-4].

Continuing, a benzene solution containing the above-mentioned Compound [3-4] was allowed to stand for 10 minutes at 25° C. under protection from light by discontinuing irradiation with visible light. The absorption spectrum of the benzene solution while in this state was then measured by ultraviolet-visible absorption spectroscopy. The results are shown in Table 2 and FIG. 15. Furthermore, these results are indicated with the broken line in FIG. 15.

Figure 15:
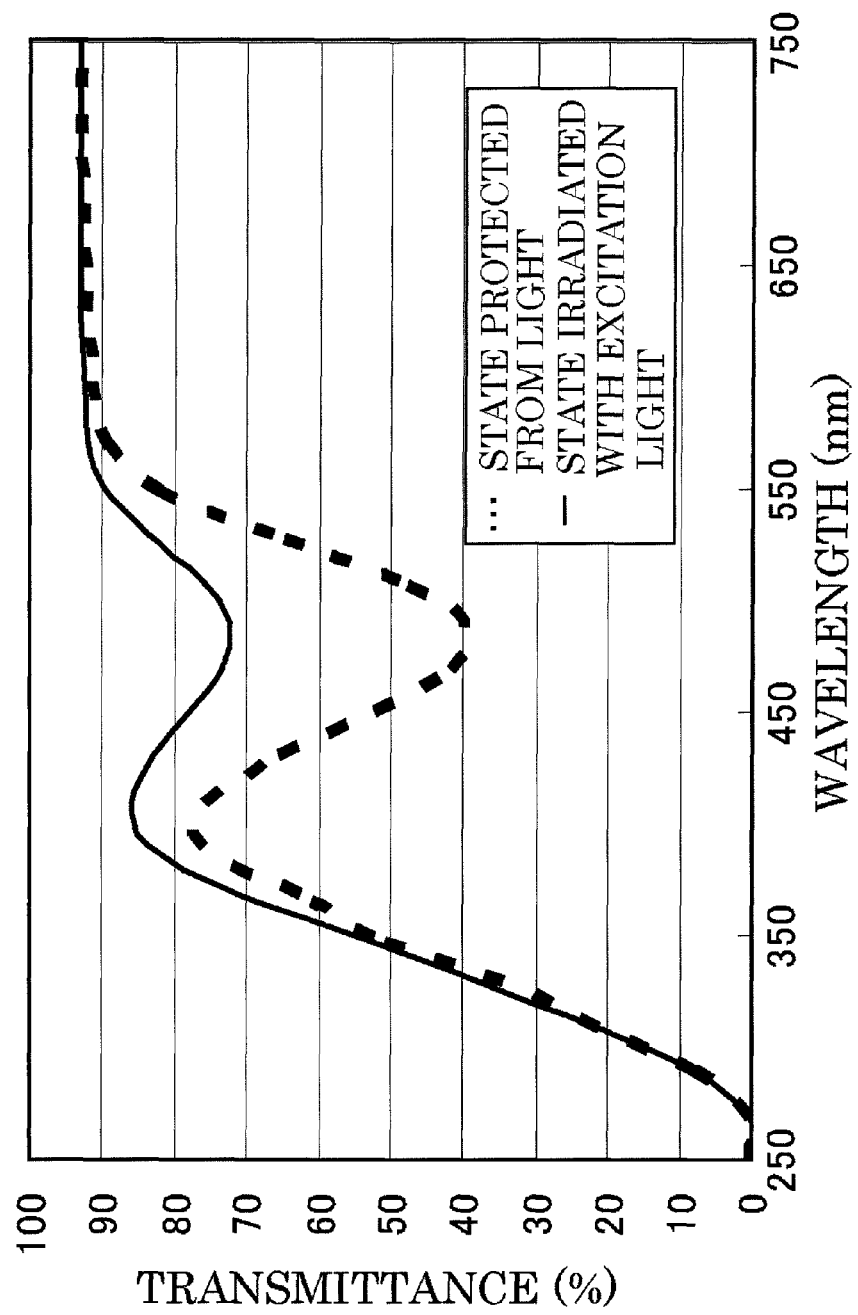
FIG. 15 is a graph showing the ultraviolet-visible light absorption spectra of a compound [3-4] according to Example 3-5 when irradiated with light and when protected from light.

As is shown in Table 2 and FIG. 15, transmittance of the uncolored form at the wavelength of maximum absorbance of the colored form of 486 nm was determined to have decreased from 74% to 39% as a result of allowing to stand under protection from light. In addition, the absorption spectrum indicated with the broken line in FIG. 15 was similar to the absorption spectrum of Compound [1-5]. On the basis thereof, Compound [3-4] was determined to have changed to Compound [1-5] as a result of allowing to stand under protection from light.

Comparative Example 3-1

A $2.0 \times 10^{-4}$ M benzene solution was prepared using Compound [1-6] synthesized in Synthesis Example 1-6. This solution was placed in a rectangular quartz cell and irradiated with visible light for 30 seconds at 25° C.

The absorption spectrum of the above-mentioned benzene solution was measured by ultraviolet-visible absorption spectroscopy while continuing to irradiate with visible light. The results are shown in Table 2 and FIG. 16. Furthermore, these results are indicated with the solid line in FIG. 16.

Continuing, a benzene solution containing the above-mentioned Compound [1-6] was allowed to stand for 10 minutes at 25° C. under protection from light by discontinuing irradiation with visible light. The absorption spectrum of the benzene solution while in this state was then measured by ultraviolet-visible absorption spectroscopy. The results are shown in Table 2 and FIG. 16. Furthermore, these results are indicated with the broken line in FIG. 16.

Figure 16:
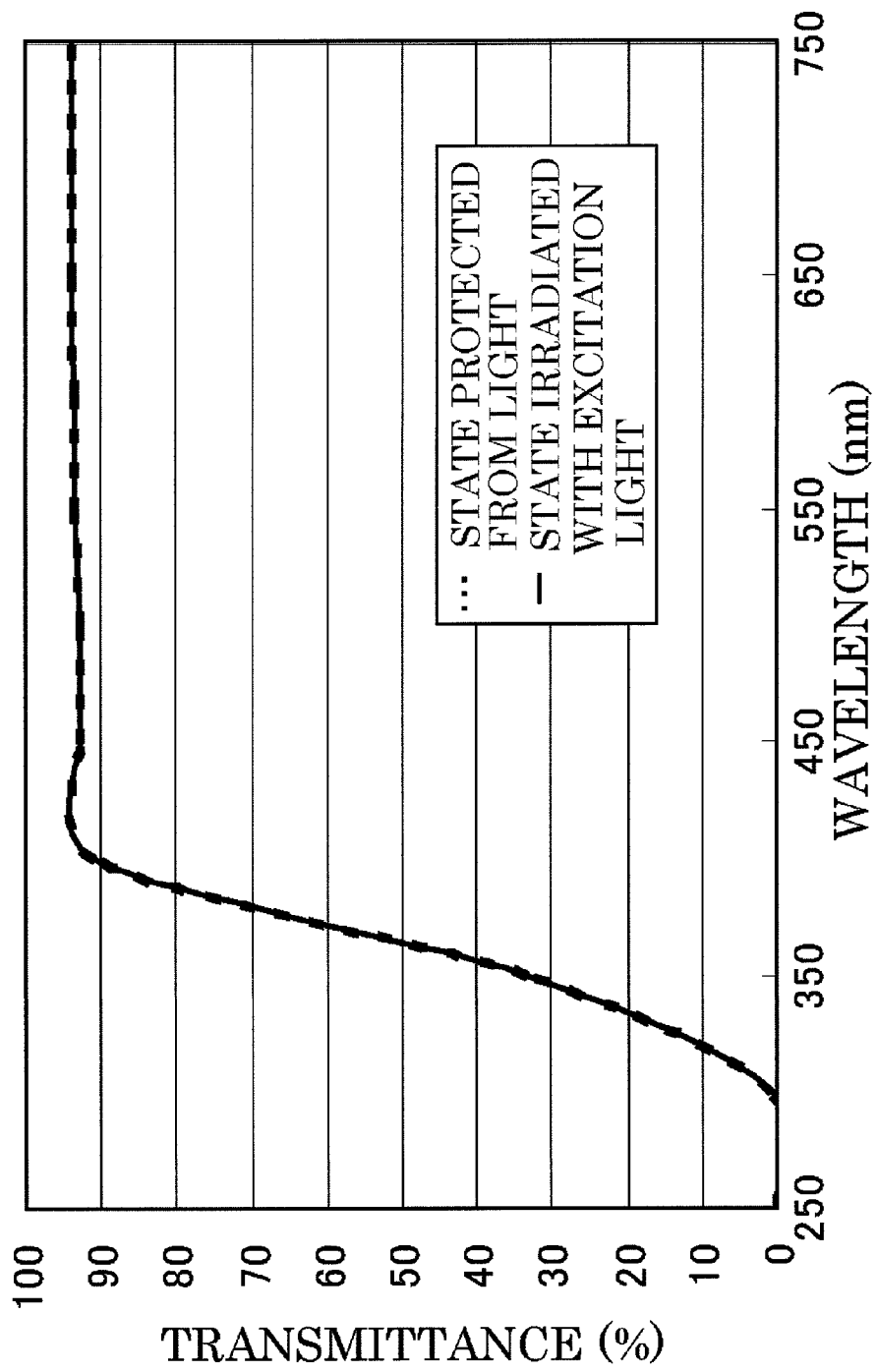
FIG. 16 is a graph showing the ultraviolet-visible light absorption spectra of a compound [1-6] according to Comparative Example 3-1 when irradiated with light and when protected from light.

As is shown in Table 2 and FIG. 16, transmittance of the uncolored form at 500 nm was determined to not have changed from 93% even if allowed to stand under protection from light. On the basis thereof, Compound [1-6] was determined to not change even if allowed to stand under protection from light.

TABLE 2

| | Wavelength of maximum absorbance of colored form (nm) | Transmittance of uncolored form (%) | Transmittance of colored form (%) |
|---|---|---|---|
| Example 3-1 | 496 | 93 | 60 |
| Example 3-2 | 493 | 88 | 17 |
| Example 3-3 | 475 | 73 | 16 |
| Example 3-4 | 544 | 74 | 23 |
| Example 3-5 | 486 | 74 | 39 |
| Comparative Example 3-1 | 500 | 93 | 93 |

According to the results shown in Table 2, molecules demonstrating photochromic properties were determined to be obtained by introducing sterically bulky substituents into $R_4$ and $R_5$ of a biimidazole compound represented by general formula (3-1).

INDUSTRIAL APPLICABILITY

The photochromic material of the present invention demonstrates photochromic properties indicated in (1), (2) or (3) below.

(1) Photochromic properties such that the photochromic material demonstrates red to violet color, is sensitive to visible light, and demonstrates a large increase in transmittance as a result of absorbing light.

(2) Photochromic properties such that the photochromic material demonstrates a large decrease in transmittance as a result of absorbing light.

(3) Photochromic properties such that the photochromic material demonstrates a large decrease in transmittance as a result of allowing to stand under protection from light.

The photochromic material of the present invention can be applied in fields such as optical switches, printing materials or recording materials, for which their application has been proposed in the past, by utilizing the above-mentioned properties of (1) to (3). For example, in the case of using as a mask layer material of an optical memory element, favorable reproduced signals can be obtained from high-density recorded bits without causing deterioration of the reproduced signals. Moreover, since the photochromic material of the present invention has a structure that is completely different from conventional molecules demonstrating photochromism, it provides a new choice when developing devices that utilize photochromism.

The invention claimed is:
1. A photochromic material formed of a biimidazole compound represented by the following formula (1-1):

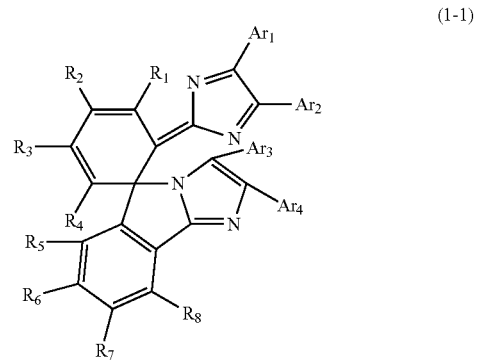

(1-1)

(where, $R_4$ and $R_5$ respectively and independently represent a halogen atom or alkyl group, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, $Ar_1$ to $Ar_4$ respectively and independently represent a substituted or unsubstituted aryl group, or $R_4$ may form a condensed, substituted or unsubstituted aryl ring with $R_3$, and $R_5$ may form a condensed, substituted or unsubstituted aryl ring with $R_6$).

2. The photochromic material according to claim 1 represented by the following formula (1-2), wherein, in the formula (1-1), $R_4$ and $R_5$ are methyl groups:

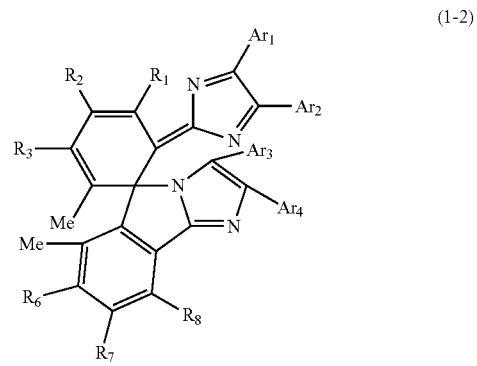

(1-2)

(where, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, and $Ar_1$ to $Ar_4$ respectively and independently represent a substituted or unsubstituted aryl group).

3. The photochromic material according to claim 1 represented by the following formula (1-3), wherein, in the formula (1-1), $R_4$ forms a condensed, substituted or unsubstituted benzene ring with $R_3$, and $R_5$ forms a condensed, substituted or unsubstituted benzene ring with $R_6$:

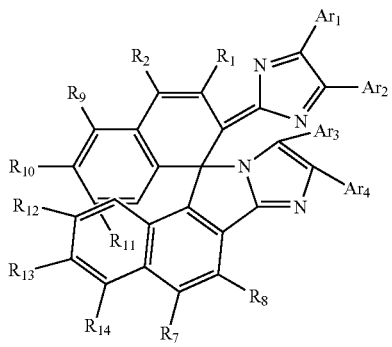

(1-3)

(where, $R_1$ and $R_2$ as well as $R_7$ to $R_{14}$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, and $Ar_1$ to $Ar_4$ respectively and independently represent a substituted or unsubstituted aryl group).

4. A photochromic material formed of a biimidazole compound represented by the following formula (2-1):

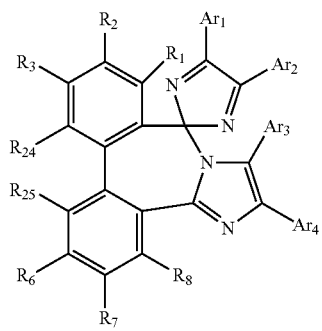

(2-1)

(where, $R_{24}$ and $R_{25}$ respectively and independently represent an alkyl group or an alkyl group having a substituent, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, and $Ar_i$ to $Ar_4$ respectively and independently represent a substituted or unsubstituted aryl group).

5. The photochromic material according to claim 4 represented by the following formula (2-2), wherein, in the formula (2-1), $R_{24}$ and $R_{25}$ are methyl groups:

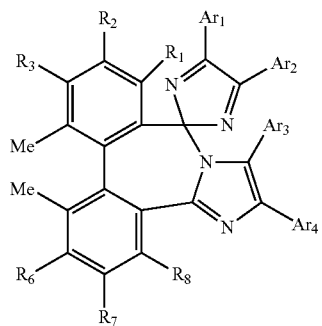

(2-2)

(where, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, and $Ar_1$ to $Ar_4$ respectively and independently represent a substituted or unsubstituted aryl group).

6. A photochromic material formed of a biimidazole compound represented by the following formula (3-1):

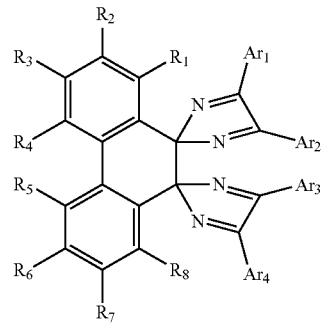

(3-1)

(where, $R_4$ and $R_5$ respectively and independently represent a halogen atom or alkyl group, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, $Ar_1$ to $Ar_4$ respectively and independently represent a substituted or unsubstituted aryl group, or $R_4$ may form a condensed, substituted or unsubstituted aryl ring with $R_3$, and $R_5$ may form a condensed, substituted or unsubstituted aryl ring with $R_6$).

7. The photochromic material according to claim 6 represented by the following formula (3-2), wherein, in the formula (3-1), $R_4$ and $R_5$ are methyl groups:

(3-2)

(where, $R_1$ to $R_3$ and $R_6$ to $R_8$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, and $Ar_1$ to $Ar_4$ respectively and independently represent a substituted or unsubstituted aryl group).

8. The photochromic material according to claim 6 represented by the following formula (3-3), wherein, in the formula (3-1), $R_4$ forms a condensed, substituted or unsubstituted benzene ring with $R_3$, and $R_5$ forms a condensed, substituted or unsubstituted benzene ring with $R_6$:

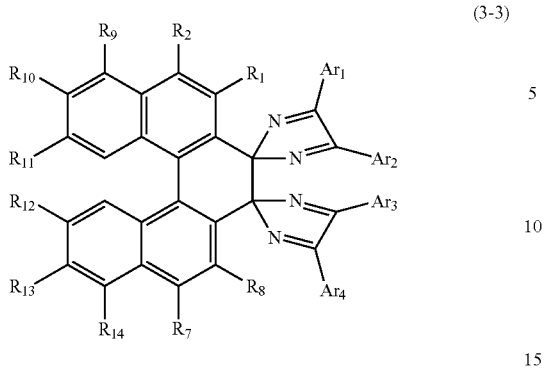

(where, $R_1$ and $R_2$ as well as $R_7$ to $R_{14}$ respectively and independently represent a hydrogen atom, halogen atom, alkyl group, fluoroalkyl group, hydroxyl group, alkoxyl group, amino group, alkylamino group, alkylcarbonyl group, nitro group, cyano group or aryl group, and $Ar_1$ to $Ar_4$ respectively and independently represent a substituted or unsubstituted aryl group).

* * * * *